(12) United States Patent
Leng et al.

(10) Patent No.: US 11,732,286 B2
(45) Date of Patent: Aug. 22, 2023

(54) T5 EXONUCLEASE-BASED METHOD TO IDENTIFY DNA TOPOISOMERASE INHIBITORS

(71) Applicants: Fenfei Leng, Palmetto Bay, FL (US); Zifang Deng, Miami, FL (US)

(72) Inventors: Fenfei Leng, Palmetto Bay, FL (US); Zifang Deng, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 5 days.

(21) Appl. No.: 17/670,738

(22) Filed: Feb. 14, 2022

(65) Prior Publication Data

US 2022/0170070 A1 Jun. 2, 2022

Related U.S. Application Data

(63) Continuation of application No. 17/343,918, filed on Jun. 10, 2021, now Pat. No. 11,268,129, which is a continuation of application No. 17/072,502, filed on Oct. 16, 2020, now Pat. No. 11,286,514.

(51) Int. Cl.

| | |
|---|---|
| *C12Q 1/68* | (2018.01) |
| *C07H 21/00* | (2006.01) |
| *C12Q 1/533* | (2006.01) |
| *C12Q 1/44* | (2006.01) |
| *G01N 21/64* | (2006.01) |

(52) U.S. Cl.
CPC ............... *C12Q 1/533* (2013.01); *C12Q 1/44* (2013.01); *G01N 21/6428* (2013.01); *G01N 2021/6439* (2013.01); *G01N 2500/04* (2013.01); *G01N 2500/20* (2013.01)

(58) Field of Classification Search
CPC .............................. C12Q 1/6818; C07H 21/00
See application file for complete search history.

(56) References Cited

U.S. PATENT DOCUMENTS

| | | |
|---|---|---|
| 9,890,416 B2 | 2/2018 | Leng |
| 10,150,987 B2 | 12/2018 | Leng |
| 2013/0090355 A1 | 4/2013 | Bresnick |

OTHER PUBLICATIONS

Cui, H. Helen et al. "Fluorescence lifetime-based discrimination and quantification of cellular DNA and RNA with phase-sensitive flow cytometry," Cytometry Part A vol. 52A, Issue 1, pp. 46-55, published Feb. 20, 2003.

*Primary Examiner* — Maryam Monshipouri
(74) *Attorney, Agent, or Firm* — Saliwanchik, Lloyd & Eisenschenk

(57) ABSTRACT

The present invention provides assays and methods for studying DNA topology and topoisomerases. The assays and methods utilize a circular plasmid DNA comprising one or more hairpin structures and the ability of T5 exonuclease (T5E) to digest the circular plasmid DNA in a specific configuration. The assays and methods can be used as a high throughput screening for inhibitors of, for example, DNA gyrases and DNA topoisomerases I for anticancer drug and antibiotics discovery.

12 Claims, 13 Drawing Sheets

Specification includes a Sequence Listing.

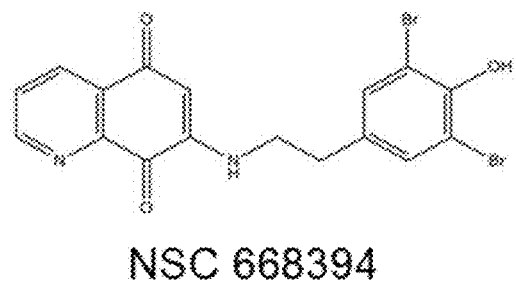
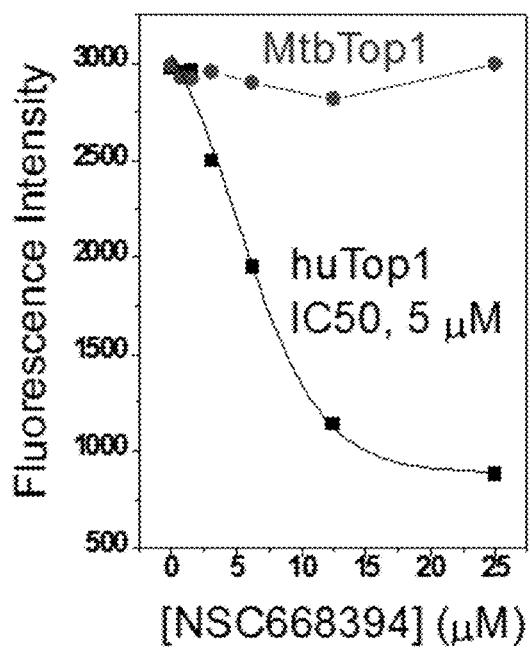
FIG. 14A
FIG. 14B
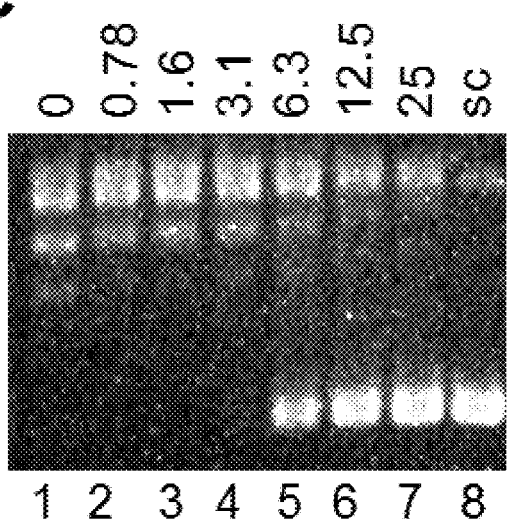
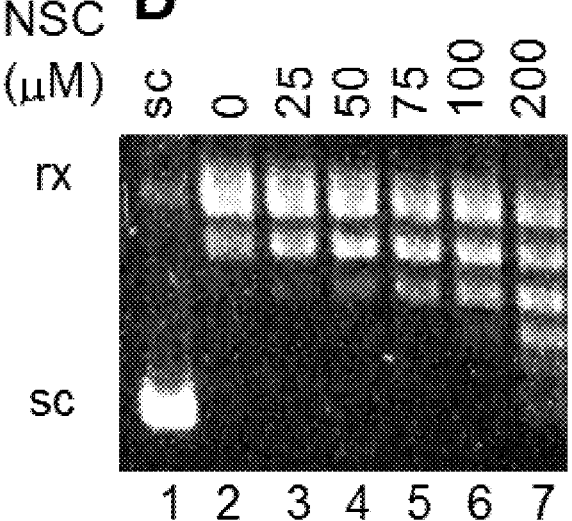
FIG. 14C
FIG. 14D

SEQUENCE LISTING

```
<160> NUMBER OF SEQ ID NOS: 2

<210> SEQ ID NO 1
<211> LENGTH: 2757
<212> TYPE: DNA
<213> ORGANISM: Artificial sequence
<220> FEATURE:
<223> OTHER INFORMATION: top strand of the plasmid pAB1

<400> SEQUENCE: 1
tcagcggatc cccgggtacc gagctcgaat tcgtaatcat ggtcatagct gtttcctgtg     60
tgaaattgtt atccgctcac aattccacac aacatacgag ccggaagcat aaagtgtaaa    120
gcctggggtg cctaatgagt gagctaactc acattaattg cgttgcgctc actgcccgct    180
ttccagtcgg gaaacctgtc gtgccagctg cattaatgaa tcggccaacg cgcggggaga    240
ggcggtttgc gtattgggcg ctcttccgct tcctcgctca ctgactcgct gcgctcggtc    300
gttcggctgc ggcgagcggt atcagctcac tcaaaggcgg taatacggtt atccacagaa    360
tcaggggata acgcaggaaa gaacatgtga gcaaaaggcc agcaaaaggc caggaaccgt    420
aaaaaggccg cgttgctggc gtttttccat aggctccgcc cccctgacga gcatcacaaa    480
aatcgacgct caagtcagag gtggcgaaac ccgacaggac tataaagata ccaggcgttt    540
ccccctggaa gctccctcgt gcgctctcct gttccgaccc tgccgcttac cggatacctg    600
tccgcctttc tcccttcggg aagcgtggcg ctttctcata gctcacgctg taggtatctc    660
agttcggtgt aggtcgttcg ctccaagctg ggctgtgtgc acgaaccccc cgttcagccc    720
gaccgctgcg ccttatccgg taactatcgt cttgagtcca acccggtaag acacgactta    780
tcgccactgg cagcagccac tggtaacagg attagcagag cgaggtatgt aggcggtgct    840
acagagttct tgaagtggtg gcctaactac ggctacacta gaaggacagt atttggtatc    900
tgcgctctgc tgaagccagt taccttcgga aaaagagttg gtagctcttg atccggcaaa    960
```

```
caaaccaccg ctggtagcgg tggttttttt gtttgcaagc agcagattac gcgcagaaaa    1020
aaaggatctc aagaagatcc tttgatcttt tctacggggt ctgacgctca gtggaacgaa    1080
aactcacgtt aagggatttt ggtcatgaga ttatcaaaaa ggatcttcac ctagatcctt    1140
ttaaattaaa aatgaagttt taaatcaatc taaagtatat atgagtaaac ttggtctgac    1200
agttaccaat gcttaatcag tgaggcacct atctcagcga tctgtctatt tcgttcatcc    1260
atagttgcct gactccccgt cgtgtagata actacgatac gggagggctt accatctggc    1320
cccagtgctg caatgatacc gcgagaccca cgctcaccgg ctccagattt atcagcaata    1380
aaccagccag ccgaagggc cgagcgcaga agtggtcctg caactttatc cgcctccatc    1440
cagtctatta attgttgccg ggaagctaga gtaagtagtt cgccagttaa tagtttgcgc    1500
aacgttgttg ccattgctac aggcatcgtg gtgtcacgct cgtcgtttgg tatggcttca    1560
ttcagctccg gttcccaacg atcaaggcga gttacatgat cccccatgtt gtgcaaaaaa    1620
gcggttagct ccttcggtcc tccgatcgtt gtcagaagta agttggccgc agtgttatca    1680
ctcatggtta tggcagcact gcataattct cttactgtca tgccatccgt aagatgcttt    1740
tctgtgactg gtgagtactc aaccaagtca ttctgagaat agtgtatgcg gcgaccgagt    1800
tgctcttgcc cggcgtcaat acgggataat accgcgccac atagcagaac tttaaaagtg    1860
ctcatcattg gaaaacgttc ttcggggcga aaactctcaa ggatcttacc gctgttgaga    1920
tccagttcga tgtaacccac tcgtgcaccc aactgatctt cagcatcttt tactttcacc    1980
agcgtttctg ggtgagcaaa aacaggaagg caaaatgccg caaaaaaggg aataagggcg    2040
acacggaaat gttgaatact catactcttc ctttttcaat attattgaag catttatcag    2100
ggttattgtc tcatgagcgg atacatattt gaatgtattt agaaaaataa acaaataggg    2160
gttccgcgca catttccccg aaaagtgcca cctgacgtct aagaaaccat tattatcatg    2220
acattaacct ataaaaatag gcgtatcacg aggccctttc gtctcgcgcg tttcggtgat    2280
gacggtgaaa acctctgaca catgcagctc ccggagacgg tcacagcttg tctgtaagcg    2340
gatgccggga gcagacaagc ccgtcagggc gcgtcagcgg gtgttggcgg gtgtcggggc    2400
tggcttaact atgcggcatc agagcagatt gtactgagag tgcaccatat gcggtgtgaa    2460
ataccgcaca gatgcgtaag gagaaaatac cgcatcaggc gccattcgcc attcaggctg    2520
cgcaactgtt gggaagggcg atcggtgcgg gcctcttcgc tattacgcca gctggcgaaa    2580
gggggatgtg ctgcaaggcg attaagttgg gtaacgccag ggttttccca gtcacgacgt    2640
tgtaaaacga cggccagtgc caagcttgca tgccctcagc ccgacagcac gagacgtat    2700 atatatatat atatatatat atatatatat atatatatgg gccaaccaac cagcccc     2757
```

<210> SEQ ID NO 2
<211> LENGTH: 2757
<212> TYPE: DNA
<213> ORGANISM: Artificial sequence
<220> FEATURE:
<223> OTHER INFORMATION: bottom strand of the plasmid pAB1

<400> SEQUENCE: 2

```
ggggctggtt ggttggccca tatatatata tatatatata tatatatata tatatatata      60
tcgtctcgtg ctgtcgggct gagggcatgc aagcttggca ctggccgtcg ttttacaacg     120
tcgtgactgg gaaaaccctg gcgttaccca acttaatcgc cttgcagcac atccccctt     180 cgccagctgg cgtaatagcg aagaggcccg caccgatcgc ccttcccaac agttgcgcag     240
```

```
cctgaatggc gaatggcgcc tgatgcggta ttttctcctt acgcatctgt gcggtatttc    300
acaccgcata tggtgcactc tcagtacaat ctgctctgat gccgcatagt taagccagcc    360
ccgacacccg ccaacacccg ctgacgcgcc ctgacgggct tgtctgctcc cggcatccgc    420
ttacagacaa gctgtgaccg tctccgggag ctgcatgtgt cagaggtttt caccgtcatc    480
accgaaacgc gcgagacgaa agggcctcgt gatacgccta tttttatagg ttaatgtcat    540
gataataatg gtttcttaga cgtcaggtgg cacttttcgg ggaaatgtgc gcggaacccc    600
tatttgttta ttttttctaaa tacattcaaa tatgtatccg ctcatgagac aataaccctg    660
ataaatgctt caataatatt gaaaaaggaa gagtatgagt attcaacatt tccgtgtcgc    720
ccttattccc ttttttgcgg cattttgcct tcctgttttt gctcacccag aaacgctggt    780
gaaagtaaaa gatgctgaag atcagttggg tgcacgagtg ggttacatcg aactggatct    840
caacagcggt aagatccttg agagttttcg ccccgaagaa cgttttccaa tgatgagcac    900
ttttaaagtt ctgctatgtg gcgcggtatt atcccgtatt gacgccgggc aagagcaact    960
cggtcgccgc atacactatt ctcagaatga cttggttgag tactcaccag tcacagaaaa   1020
gcatcttacg gatggcatga cagtaagaga attatgcagt gctgccataa ccatgagtga   1080
taacactgcg gccaacttac ttctgacaac gatcggagga ccgaaggagc taaccgcttt   1140
tttgcacaac atgggggatc atgtaactcg ccttgatcgt tgggaaccgg agctgaatga   1200
agccatacca aacgacgagc gtgacaccac gatgcctgta gcaatggcaa caacgttgcg   1260
caaactatta actggcgaac tacttactct agcttcccgg caacaattaa tagactggat   1320
ggaggcggat aaagttgcag gaccacttct gcgctcggcc cttccggctg gctggtttat   1380
tgctgataaa tctggagccg gtgagcgtgg gtctcgcggt atcattgcag cactggggcc   1440
agatggtaag ccctcccgta tcgtagttat ctacacgacg gggagtcagg caactatgga   1500
tgaacgaaat agacagatcg ctgagatagg tgcctcactg attaagcatt ggtaactgtc   1560
agaccaagtt tactcatata ctttagat tgatttaaaa cttcattttt aatttaaaag   1620
gatctaggtg aagatccttt ttgataatct catgaccaaa atcccttaac gtgagttttc   1680
gttccactga gcgtcagacc ccgtagaaaa gatcaaagga tcttcttgag atccttttt   1740
tctgcgcgta atctgctgct tgcaaacaaa aaaaccaccg ctaccagcgg tggtttgttt   1800
gccggatcaa gagctaccaa ctctttttcc gaaggtaact ggcttcagca gagcgcagat   1860
accaaatact gtccttctag tgtagccgta gttaggccac cacttcaaga actctgtagc   1920
accgcctaca tacctcgctc tgctaatcct gttaccagtg gctgctgcca gtggcgataa   1980
gtcgtgtctt accgggttgg actcaagacg atagttaccg gataaggcgc agcggtcggg   2040
ctgaacgggg ggttcgtgca cacagcccag cttggagcga acgacctaca ccgaactgag   2100
atacctacag cgtgagctat gagaaagcgc cacgcttccc gaagggagaa aggcggacag   2160
gtatccggta agcggcaggg tcggaacagg agagcgcacg agggagcttc caggggggaaa   2220
cgcctggtat ctttatagtc ctgtcgggtt tcgccacctc tgacttgagc gtcgattttt   2280
gtgatgctcg tcaggggggc ggagcctatg gaaaaacgcc agcaacgcgg cctttttacg   2340
gttcctggcc ttttgctggc cttttgctca catgttcttt cctgcgttat cccctgattc   2400
tgtggataac cgtattaccg cctttgagtg agctgatacc gctcgccgca gccgaacgac   2460
cgagcgcagc gagtcagtga gcgaggaagc ggaagagcgc ccaatacgca aaccgcctct   2520
ccccgcgcgt tggccgattc attaatgcag ctggcacgac aggtttcccg actggaaagc   2580
gggcagtgag cgcaacgcaa ttaatgtgag ttagctcact cattaggcac cccaggcttt   2640
```

```
acactttatg cttccggctc gtatgttgtg tggaattgtg agcggataac aatttcacac    2700
aggaaacagc tatgaccatg attacgaatt cgagctcggt acccggggat ccgctga      2757
```

T5 EXONUCLEASE-BASED METHOD TO IDENTIFY DNA TOPOISOMERASE INHIBITORS

CROSS-REFERENCE TO RELATED APPLICATIONS

This application is a continuation application of U.S. Ser. No. 17/343,918, filed Jun. 10, 2021; which is a continuation application of U.S. Ser. No. 17/072,502, filed Oct. 16, 2020, which are incorporated herein by reference in its entirety.

GOVERNMENT SUPPORT

This invention was made with government support under AI125973, awarded by the National Institutes of Health. The government has certain rights in the invention.

SEQUENCE LISTING

The Sequence Listing for this application is labeled "SeqList-16Oct20-ST20", which was created on Oct. 16, 2020, and is 8 KB. The entire content is incorporated herein by reference in its entirety.

BACKGROUND OF THE INVENTION

DNA topoisomerases (Topos) are enzymes responsible for the relaxation of (+) and (−) supercoiled (sc) DNA and the resolution of DNA knots and catenanes during essential biological processes, such as DNA replication, transcription, recombination, and maintenance of chromosome structure. These enzymes catalyze the changes in DNA topology through creating transient DNA break. DNA topology is a tightly-regulated property of the DNA double helix that affects genomic stability and influences susceptibility to cancer and certain hereditary diseases, such as fragile X syndrome and autism.

DNA Topos that control DNA topology inside cells are, thus, important targets for certain antibiotics and anticancer drugs. For example, type IIA topoisomerases cut and rejoin a double strand of DNA during catalysis. DNA gyrase and topoisomerase IV are prokaryotic type IIA topoisomerases that have been extensively explored as validated targets for antibacterial therapy in the clinic. Bacterial DNA gyrase and Topo IV are the targets of fluoroquinolones, such as ciprofloxacin, one of the most important and prescribed antibiotics. Human topoisomerases I and II are targets of clinically important anticancer drugs including camptothecin/topotecan and doxorubicin.

Bacterial DNA topoisomerase I is a type IA topoisomerase responsible for preventing excessive negative supercoiling in bacteria. At least one type IA topoisomerase is present in every bacterial pathogen to resolve topological barriers that require the cutting and rejoining of a single strand of DNA and passage of DNA through the transient break.

*Escherichia coli* topoisomerase I (EcTopI) is the most extensively studied type IA topoisomerase. Topoisomerase I function is essential for a number of bacterial pathogens including *Streptococcus pneumoniae* and *Helicobacter pylori*. There is only one type IA topoisomerase encoded by the genomes of Mycobacteria. *Mycobacterium tuberculosis* topoisomerase I (MtbTopI) has been demonstrated in genetic studies to be essential for viability both in vitro and in vivo, demonstrating that topoisomerase I is a vulnerable target in *M. tuberculosis* for chemical inhibition.

One commonly used assay to test DNA Topo activities is agarose gel electrophoresis. Agarose gel electrophoresis, however, is labor-intensive and time-consuming, and cannot be used as high throughput screening (HTS) assays. Another assay is to use fluorescently labeled DNA molecules to study DNA Topos by fluorescence resonance energy transfer (FRET) or supercoiling dependent fluorescence quenching (SDFQ) (Gu, M., Berrido, A., Gonzalez, W. G., Miksovska, J., Chambers, J. W., & Leng, F. (2016) Fluorescently labeled circular DNA molecules for DNA topology and topoisomerases. *Sci. Rep.* 6, 36006; Wang, Y., Rakela, S., Chambers, J. W., Hua, Z. C., Muller, M. T., Nitiss, J. L., Tse-Dinh, Y. C., & Leng, F. (2019) Kinetic Study of DNA Topoisomerases by Supercoiling-Dependent Fluorescence Quenching. *ACS Omega.* 4, 18413-18422; Jude, K. M., Hartland, A., & Berger, J. M. (2013) *Nucleic Acids Res.* 41, e133). However, the synthesis of this type of fluorescently labeled DNA molecules is too expensive, preventing the use of them as a regular screening agent for drug discovery. Additionally, certain potential Topo inhibitors have fluorescence that greatly interfere with the final detection signal.

Thus, there is a need to develop and/or identify agents, methods and assays to identify Topo inhibitors used as anti-cancer and antibacterial agents. Preferably, such methods and assays can be used for high throughput screening (HTS) assays.

BRIEF SUMMARY OF THE INVENTION

The subject invention provides cost effective assays and methods for high throughput screening (HTS) assays to identify potential inhibitors that target enzymes such as DNA topoisomerases (e.g., bacterial DNA topoisomerase I and DNA gyrases as well as human DNA topoisomerase I and II). DNA topoisomerases are targets of important anti-cancer drugs and antibiotics. This technology can be used to identify new topoisomerase inhibitors that can be developed into antibiotics and anticancer drugs.

In one embodiment, the assays and methods use a type of unique nucleic acid molecule, preferably, a circular double-stranded (ds) DNA molecule that has the ability to interconvert between a relaxed (rx) configuration and a supercoiled (sc) configuration, wherein the circular dsDNA molecule in the sc configuration comprises one or more hairpin structures. In one embodiment, the circular dsDNA molecule in the sc configuration comprises one or more hairpin structures in each strand.

In a preferred embodiment, the circular dsDNA molecule is a circular double-stranded plasmid that has the ability to interconvert between a relaxed (rx) configuration and a supercoiled (sc) configuration. In a specific embodiment, the circular double-stranded plasmid in the sc configuration comprises two hairpin structures. The circular double-stranded plasmid in the sc configuration comprises one hairpin structure in each strand.

In one embodiment, the circular double-stranded plasmid comprises a sequence comprising adenosine-thymidine repeats $(AT)_n$ ($n \geq 2$) in each strand. The sequence comprising (AT)n forms a hairpin structure in each strand of the circular double-stranded plasmid when the circular double-stranded plasmid is in the sc configuration.

In one embodiment, the circular double-stranded plasmid comprises at least one DNA endonuclease or exonuclease recognition site that can be recognized by a DNA endonuclease or exonuclease. Subsequently, the circular double-strand plasmid is cleaved or digested by such endonuclease or exonuclease, failing to maintain relaxed and supercoiled configurations.

In one embodiment, the assays and methods of the subject invention also take advantage of a unique property of T5 exonuclease (T5E) that initiates nucleotide removal from the 5' termini or at gaps and nicks of linear or circular dsDNA in the 5' to 3' direction. While T5E does not degrade rx DNAs, it can digest sc dsDNAs that carries a hairpin structure or contains linear and nicked DNAs.

In one embodiment, the method of the subject invention for screening/identifying inhibitors targeting a DNA topoisomerase comprises providing a sample suspected of containing an inhibitor of the DNA topoisomerase; mixing the DNA topoisomerase of interest and a circular dsDNA molecule with the sample, wherein the circular dsDNA molecule comprises two or more hairpin structures when the circular dsDNA molecule is in a sc configuration; adding T5E into the mixture; adding a signal reporter, e.g., a DNA-staining dye; and determining the presence or absence of the inhibitor based on a signal generated from the signal reporter, e.g., fluorescence, in the sample. In a specific embodiment, the sample is a sample in a high throughput screening (HTS) sample carrier.

In one embodiment, the method of the subject invention for screening/identifying inhibitors targeting a DNA topoisomerase comprises providing a sample suspected of containing an inhibitor of the DNA topoisomerase; adding a circular dsDNA molecule comprising an adenosine-thymidine dinucleotide repeat (AT)n sequence, wherein n≥2; adding the DNA topoisomerase; adding T5E; adding a dye, e.g., DNA-staining dye; and determining the presence or absence of the inhibitor based on the fluorescence in the sample.

In one embodiment, the DNA topoisomerase is selected from DNA topoisomerase I, II, III, IV, V and DNA gyrase. In a specific embodiment, the DNA topoisomerase is bacterial DNA topoisomerase I, bacterial DNA gyrase, human DNA topoisomerase I or human DNA topoisomerase II. In a preferred embodiment, the DNA topoisomerase I is E. coli topoisomerase I, Variola topoisomerase I, Mtb topoisomerase I or human DNA topoisomerase I.

In a specific embodiment, the circular double-stranded plasmid is pAB1. Plasmid pAB1 (SEQ ID NOs: 1-2) is a double-stranded circular DNA molecule that contains 2757 base pairs. It can be propagated in E. coli cells, such as DH5a, and Top10. It comprises a 42-base pair AT sequence that can form two hairpin structures when pAB1 becomes negatively supercoiled, i.e., one hairpin structure in each strand.

In one embodiment, the dye is selected from, e.g., Hoechest 33258, SYBR gold, ethidium bromide, EthD-1, and SYBR green. Preferably, the dye is ethidium bromide, or EthD-1.

In one embodiment, the subject invention provides a method for screen/identifying inhibitors of a DNA topoisomerase I, the method comprising providing a sample suspected of containing an inhibitor of the DNA topoisomerase I; adding a circular double-stranded plasmid of the subject invention, the circular double-stranded plasmid being in a supercoiled configuration and comprising one or more hairpin structures in each strand; adding a DNA topoisomerase I; adding T5E; adding a DNA-staining dye; and determining the presence or absence of the inhibitor based on the fluorescence in the sample, wherein a lower fluorescence in the sample than a control is indicative of the presence of the inhibitor of the DNA topoisomerase I, wherein the control may comprise the circular double-stranded plasmid in a relaxed conformation in the presence of the DNA topoisomerase I.

In one embodiment, the subject invention provides a method for screen/identifying inhibitors of a DNA gyrase, the method comprising providing a sample suspected of containing an inhibitor of the DNA gyrase; adding a relaxed circular double-stranded plasmid of the subject invention; adding T5E; adding a DNA-staining dye; and determining the presence or absence of the inhibitor based on the fluorescence in the sample, wherein a higher fluorescence in the sample than a control is indicative of the presence of the inhibitor of the DNA gyrase, wherein the control may comprise, for example, the circular supercoiled double-stranded plasmid in the presence of the DNA gyrase.

In one embodiment, the subject invention also provides a method for screen/identifying DNA intercalators, the method comprising providing a sample suspected of containing a DNA intercalator; adding a circular double-stranded plasmid of the subject invention, the circular double-stranded plasmid being in a supercoiled configuration and comprising one or more hairpin structures in each strand; adding T5E; adding a DNA-staining dye; and determining the presence or absence of the DNA intercalator based on the fluorescence in the sample, wherein a higher fluorescence in the sample than a control is indicative of the presence of the DNA intercalator, wherein the control may comprise the circular sc double-stranded plasmid in the absence of a DNA intercalator.

FIGS. 5A-5F show different DNA-staining dyes used in the T5 exonuclease-based screen assays. (A) 1% agarose gel to show the effects of T5 exonuclease on plasmid pAB1 in different reaction mixtures. rx and sc represent the starting plasmid pAB1 samples either relaxed or supercoiled, respectively. Hoechst 33258 (B; $\lambda_{em}$=461 nm with $\lambda_{ex}$=352 nm), SYBR Gold (C; $\lambda_{em}$=536 nm with $\lambda_{ex}$=470 nm), SYBR Green (D; $\lambda_{em}$=520 nm with $\lambda_{ex}$=497 nm), ethidium bromide (E; $\lambda_{em}$=590 nm with $\lambda_{ex}$=360 nm), and ethidium homodimer 1 (EthD1, F; $\lambda_{em}$=617 nm with $\lambda_{ex}$=528 nm) were used.

Figure 6A:
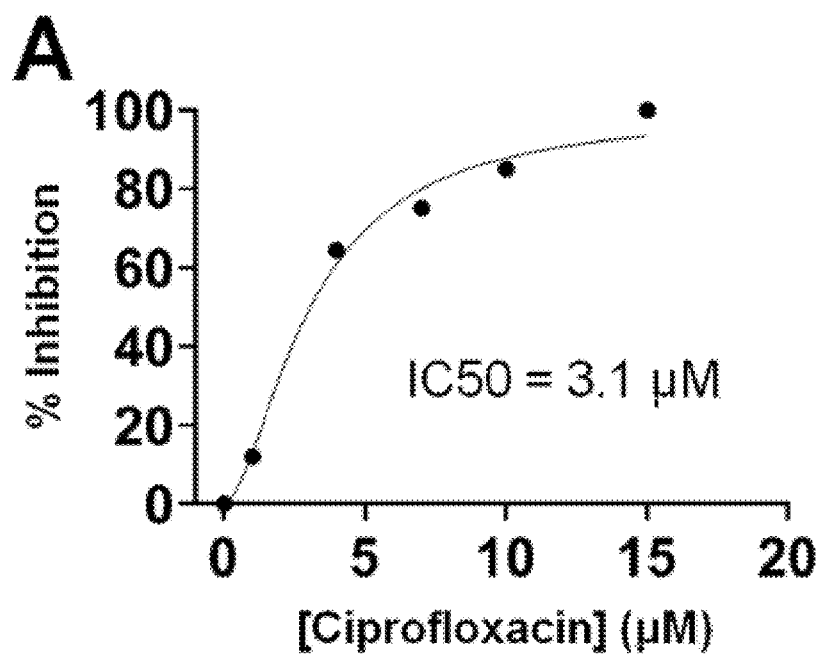
Figure 6B:
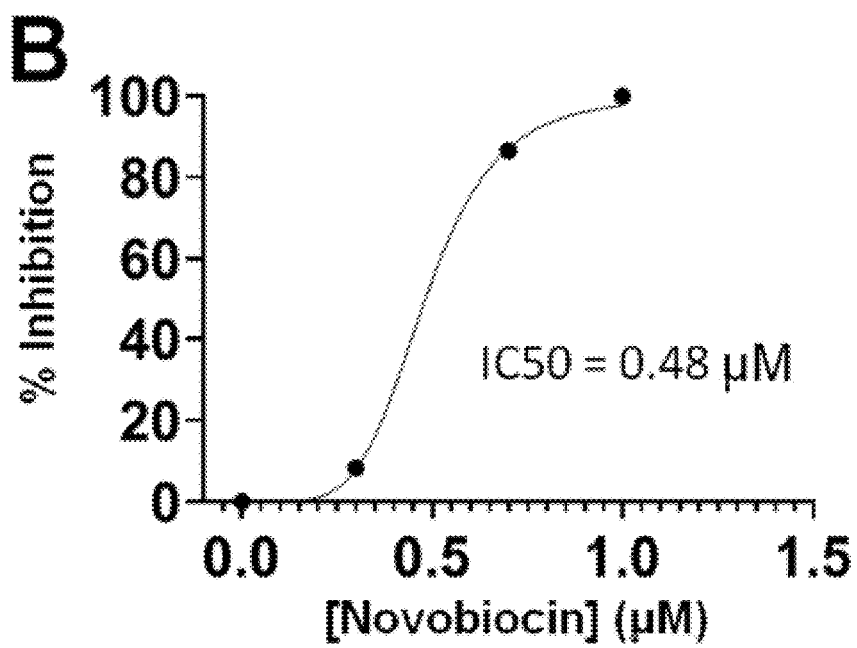

FIGS. 6A-6B show the inhibition of DNA gyrase. DNA gyrase was potently inhibited by ciprofloxacin (A) and novobiocin (B). The fluorescence intensity at $\lambda_{em}$=617 nm was monitor with $\lambda_{ex}$=528 nm. The inhibition IC50 was estimated to be 3.1 and 0.48 µM for ciprofloxacin and novobiocin, respectively.

Figure 7:
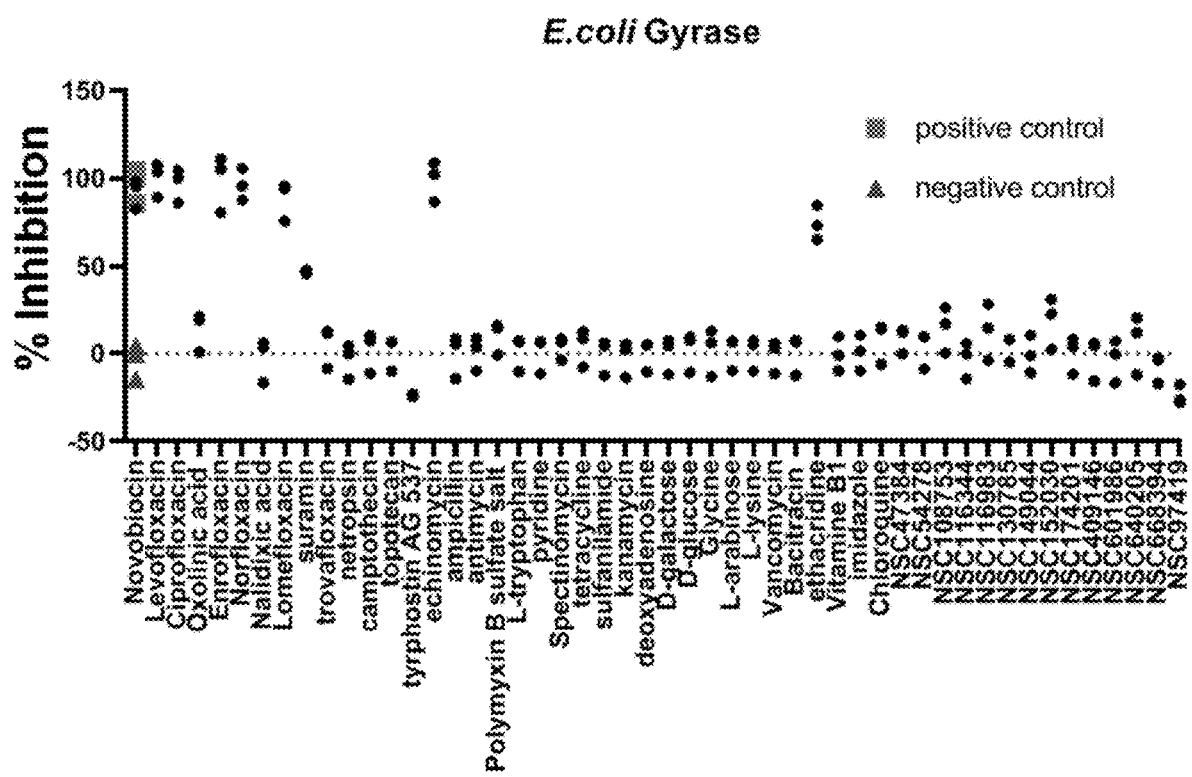

FIG. 7 shows the HTS screen of the 50-compound library for E. coli DNA gyrase inhibitors in triplicate. The library includes novobiocin, levofloxacin, ciprofloxacin, enrofloxacin, norfloxacin, lomefloxacin, suramin, echinomycin, ethacridine, ocolinic acid, nalidixic acid, trovafloxacin, netropsin, camptothecin, topotecan, tyrphostin AG 537, ampicillin, antimycin, polymyxin B sulfate salt, L-tryptophan, pyridine, spectinomycin, tetracycline, sulfanilamide, kanamycin, deoxyadenosine, D-galactose, D-glucose, glycine, L-arabinose, L-lysine, vancomycin, bacitracin, vitamin B1, imidazole, chloroquine, NSC47384, NSC54278, NSC108753, NSC116344, NSC116983, NSC130785, NSC149044, NSC152030, NSC174201, NSC409146, NSC601986, NSC640205, NSC668394, and NSC97419.

Figure 8:
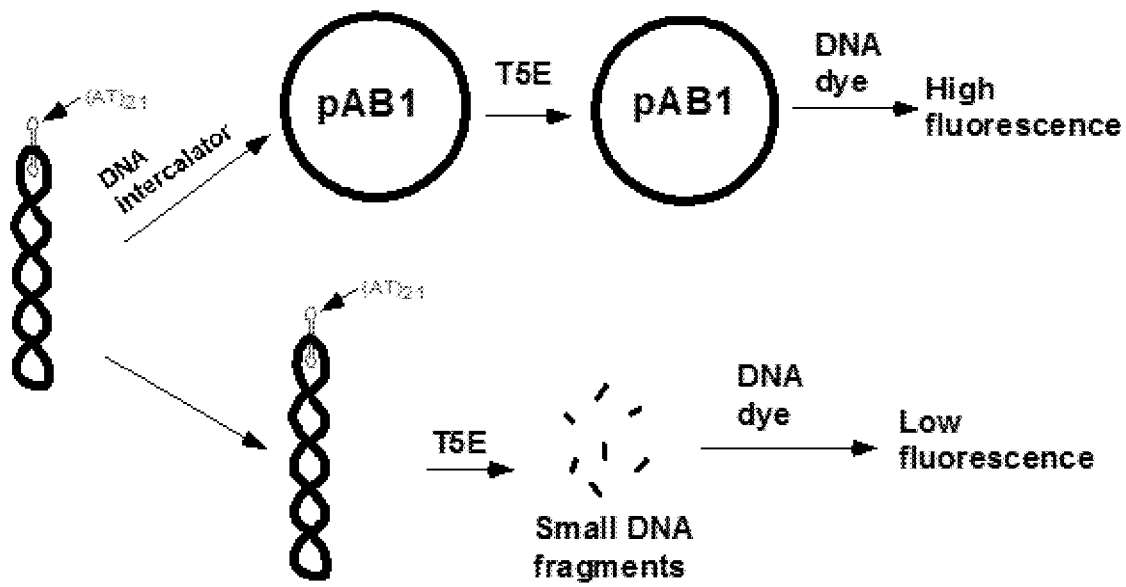

FIG. 8 shows a strategy to identify DNA intercalators by the T5 exonuclease based method.

Figure 9A:
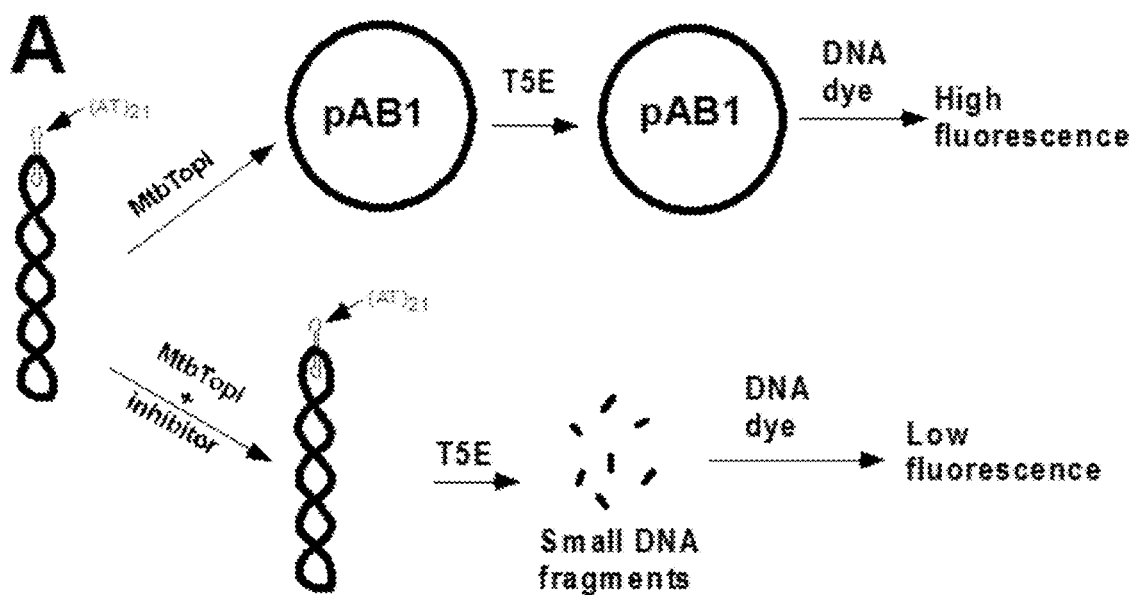
Figure 9B:
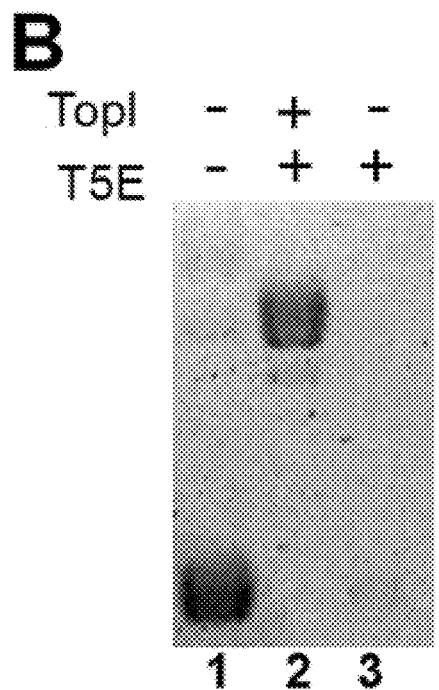
Figure 9C:
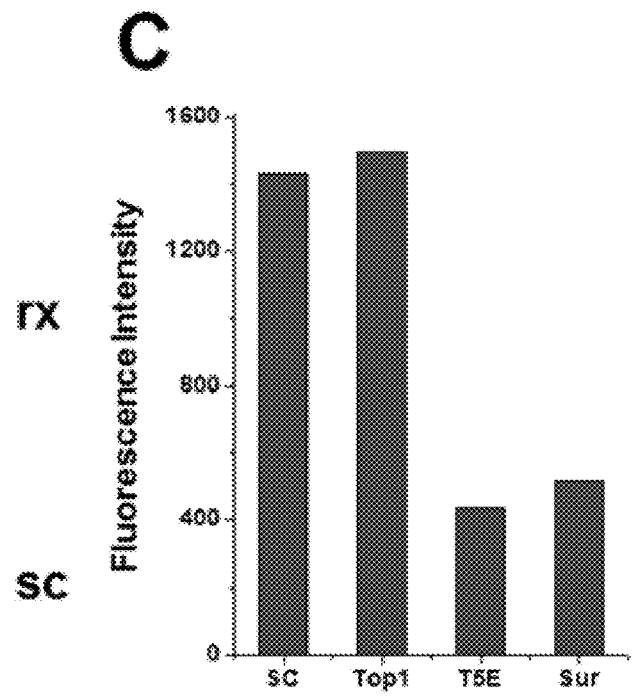

FIGS. 9A-9C show a T5 exonuclease based assay to identify MtbTopI inhibitors. (A) The experimental strategy to screen MtbTopI inhibitors. (B) T5 exonuclease (T5E) can completely digest sc pAB1 (lane 3), but not rx pAB1 (lane 2). (C) The DNA-staining dye ethidium homodimer 1 (EthD1) was added to the DNA samples. The fluorescence was measured at $\lambda_{em}$ of 617 nm with $\lambda_{ex}$=528 nm using a plate reader. SC, TopoI, and T5 are DNA samples of lanes 1-3 FIG. 9B, respectively. Sur represents suramin, a DNA topoisomerase inhibitor.

Figure 10:
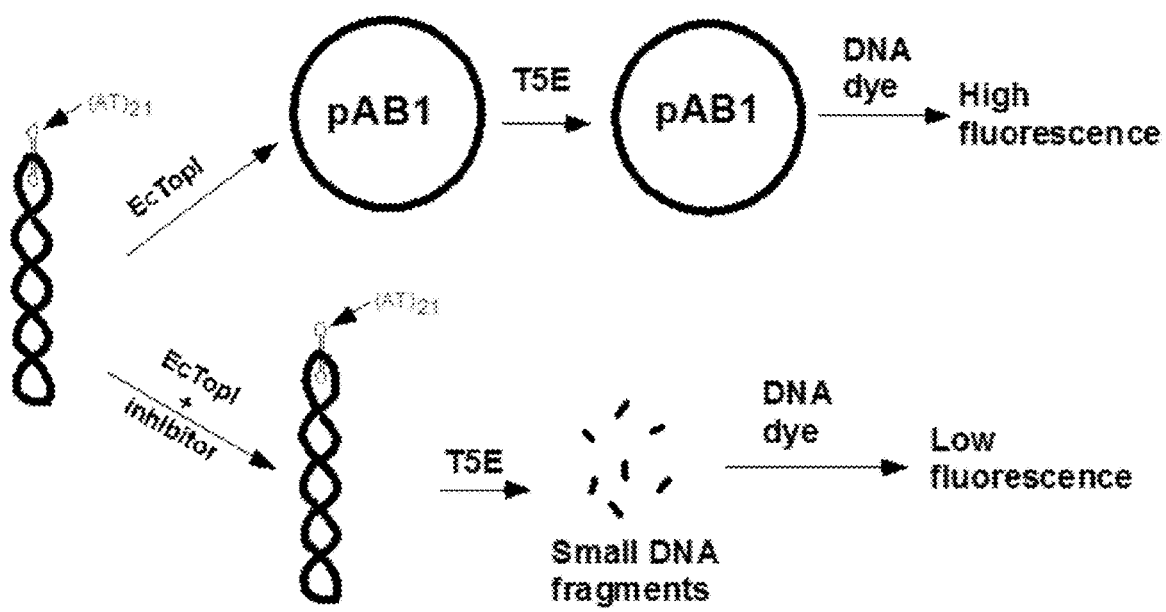

FIG. 10 shows a strategy to identify inhibitors of E. coli DNA topo I by the T5 exonuclease based method.

Figure 11:
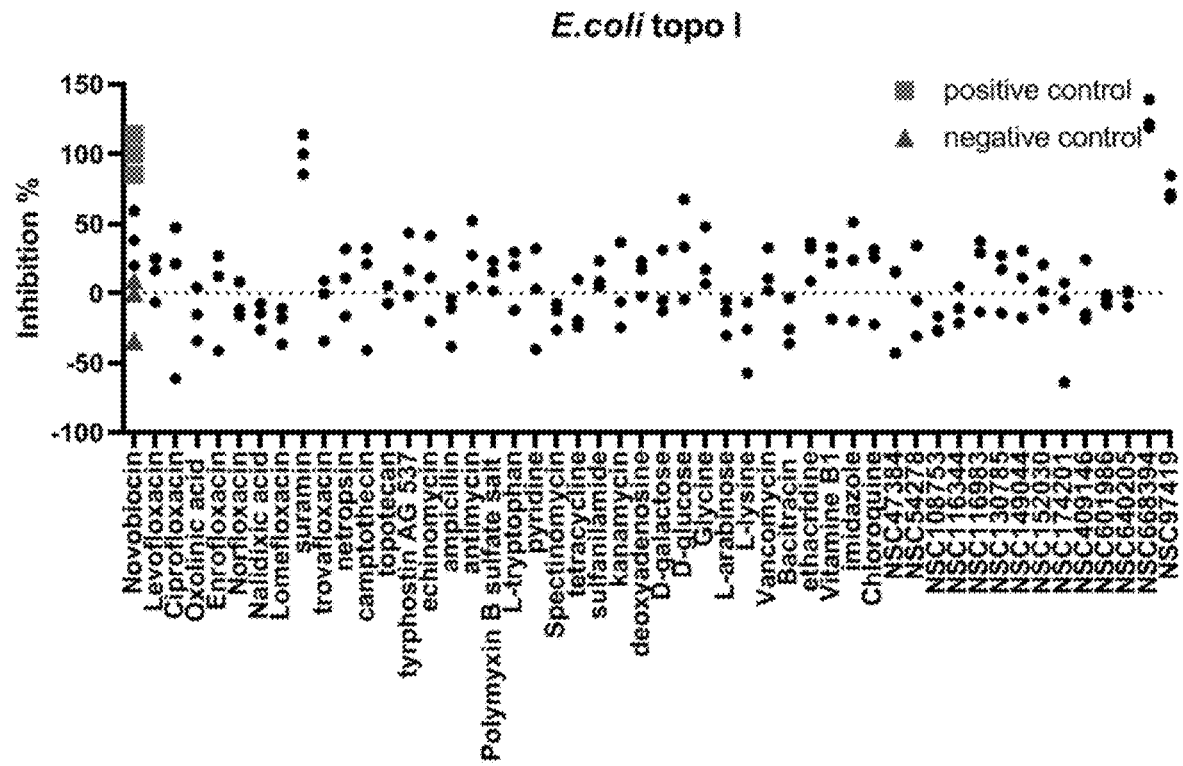

FIG. 11 shows the HTS screen of 50 compound library for E. coli topo I inhibitors in triplicate.

Figure 12:
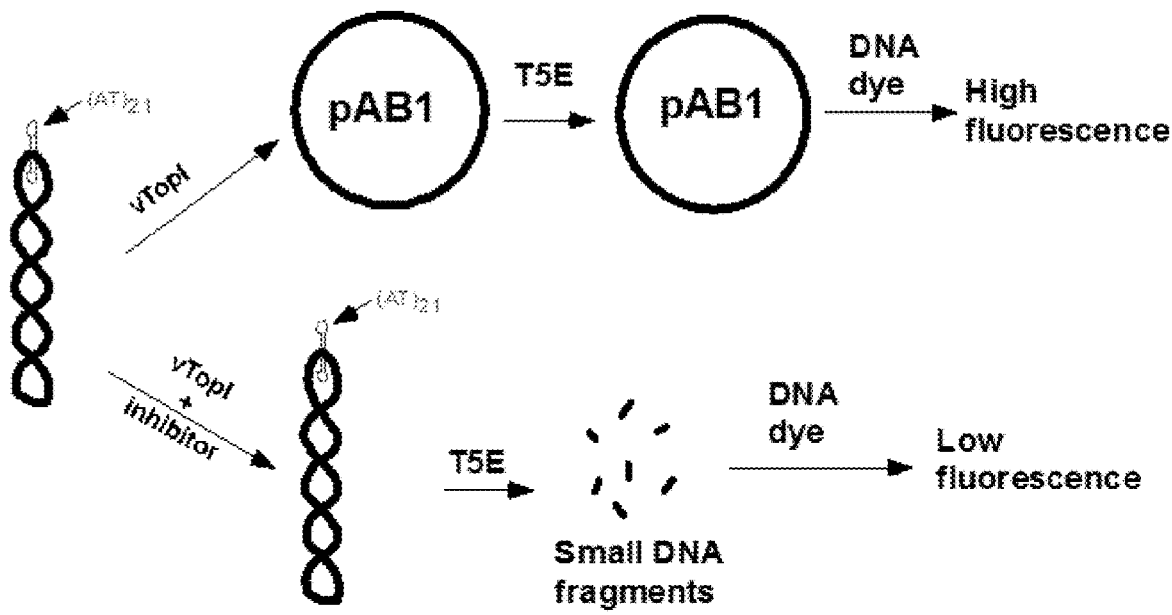

FIG. 12 shows a strategy for identifying inhibitors of Variola virus DNA topo I by the T5 exonuclease based method.

Figure 13A:
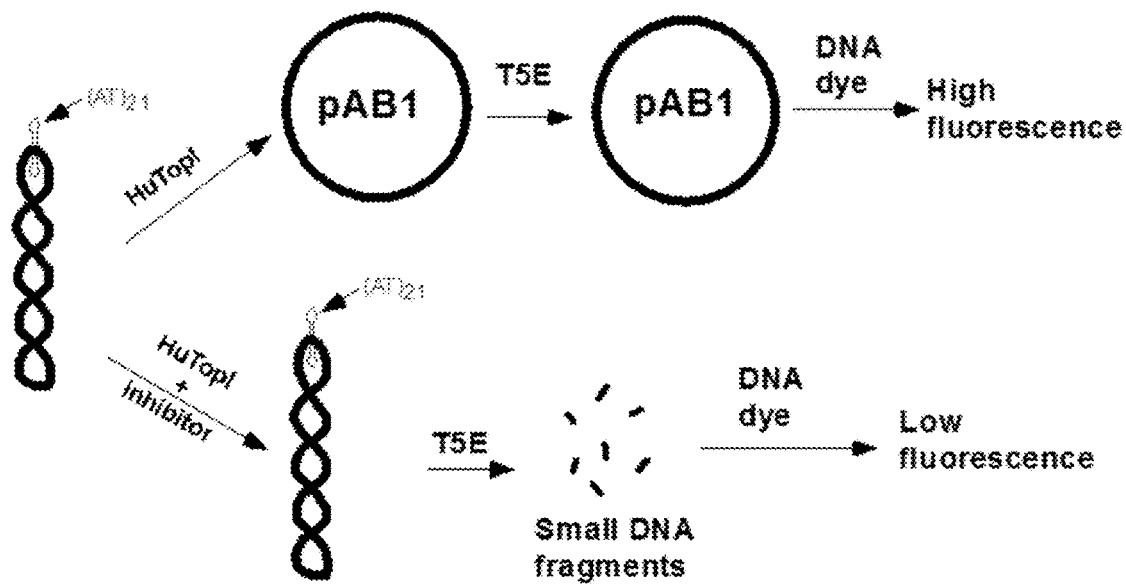
Figure 13B:
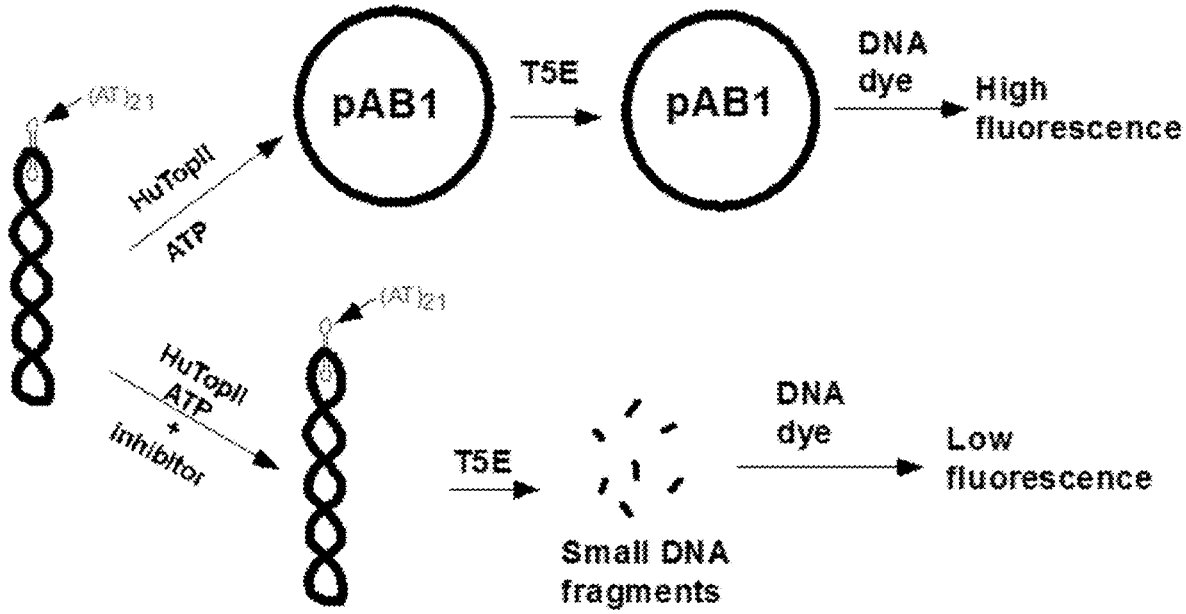

FIGS. 13A-13B show strategies for identifying inhibitors of human DNA topoisomerase I (HuTopI) (A) and DNA topoisomerase II (HuTopII) (B) by the T5 exonuclease based method.

FIGS. 14A-14D show that NSC668394 inhibits HuTopI but not MtbTopI. (A) Chemical structure of NSC668394, a new human DNA topoisomerase I inhibitor. (B) Compound NSC668394 potently inhibited HuTopI with an IC50 of 5 µM. It did not inhibit MtbTop1. The human TopI-catalyzed DNA relaxations were monitored. 60 µL of 1×huTopI Buffer (10 mM Tris-Cl, pH 7.9, 150 mM NaCl, 0.1% BSA, 0.1 mM Spermidine, 5% glycerol) containing two different concentrations of sc pAB1_FL905 was prepared. 25 nM of huTopI was used to relax the sc pAB1_FL905. The fluorescence intensity at $\lambda_{em}$=521 nm was monitor using a Biotek Synergy HI Hybrid Plate Reader with $\lambda_{ex}$=482 nm. (C) NSC668394 inhibited human topI activities. (D) NSC668394 did not inhibit MtbTop1.

BRIEF DESCRIPTION OF THE SEQUENCES

SEQ ID NO: 1 is a DNA sequence of the top strand of the plasmid pAB1 contemplated for use according to the subject invention.

SEQ ID NO: 2 is a DNA sequence of the bottom strand of the plasmid pAB1 contemplated for use according to the subject invention.

DETAILED DESCRIPTION OF THE INVENTION

The subject invention provides cheap or cost-effective and sensitive assays and methods for screening or identifying inhibitors that target the DNA topology-affecting enzymes such as DNA topoisomerases (e.g., bacterial DNA topoisomerase I, and DNA gyrases), from a compound library comprising a large number of compounds. DNA topoisomerases are targets of anticancer drugs and antibiotics. This technology can be used to identify new topoisomerase inhibitors that can be developed into antibiotics and anticancer drugs.

In one embodiment, the assays and methods use a type of unique nucleic acid molecule, preferably, a circular double-stranded (ds) DNA molecule that has the ability to interconvert between a relaxed (rx) configuration and a supercoiled (sc) configuration. Advantageously, such nucleic acid molecules can be used for fast detection of changes in DNA topology due to the ability to convert from the sc conformation to the rx conformation.

In one embodiment, the circular dsDNA molecule upon supercoiling undergoes structural changes including the formation of hairpin structures and/or cruciform structures. In a further embodiment, the circular dsDNA molecule comprises two or more hairpin/cruciform structures. Specifically, the circular dsDNA molecule in the sc configuration comprises one or more hairpin/cruciform structures in each strand.

In one embodiment, the circular double-stranded DNA molecule is a circular double-stranded plasmid that has the ability to interconvert between a relaxed (rx) configuration and a supercoiled (sc) configuration. The circular double-stranded plasmid in the sc configuration comprises two or more hairpin/cruciform structures. In a specific embodiment, the circular double-stranded plasmid in the se configuration comprises one hairpin/cruciform structure in each strand.

In certain embodiments, the circular double-stranded plasmid may comprise, for example, about 1000 base pairs to 100,000 base pairs, about 1000 base pairs to 50,000 base pairs, about 1000 base pairs to 20,000 base pairs, about 1000 base pairs to 10,000 base pairs, about 1000 base pairs to 5000 base pairs, about 1000 base pairs to 4000 base pairs, about 1000 base pairs to 3000 base pairs, about 1500 base pairs to 3000 base pairs, or about 2000 base pairs to 3000 base pairs.

In one embodiment, the hairpin/cruciform structure in a single strand of the circular double-stranded plasmid may be formed by a sequence comprising, or consisting of, about 7 nucleotides to about 200 nucleotides, about 7 nucleotides to about 150 nucleotides, about 10 nucleotides to about 120 nucleotides, about 20 nucleotides to about 100 nucleotides, about 20 nucleotides to about 90 nucleotides, about 20 nucleotides to about 80 nucleotides, about 20 nucleotides to about 70 nucleotides, about 20 nucleotides to about 60 nucleotides, about 30 nucleotides to about 60 nucleotides, about 30 nucleotides to about 50 nucleotides, or about 40 nucleotides to about 50 nucleotides.

In one embodiment, the hairpin/cruciform structure in each strand of the circular double-stranded plasmid may comprise a stem comprising, or consisting of, a 2 base pairs to 50 base pairs, 2 base pairs to 40 base pairs, 2 base pairs to 30 base pairs, 2 base pairs to 20 base pairs, 2 base pairs to 10 base pairs, 5 base pairs to 50 base pairs, 5 base pairs to 40 base pairs, 5 base pairs to 30 base pairs, 5 base pairs to 20 base pairs, 10 base pairs to 50 base pairs, 10 base pairs to 40 base pairs, 10 base pairs to 30 base pairs, 10 base pairs to 20 base pairs, 20 base pairs to 50 base pairs, 20 base pairs to 40 base pairs, 20 base pairs to 30 base pairs, 30 base pairs to 50 base pairs, or 30 base pairs to 40 base pairs.

In one embodiment, the circular double-stranded plasmid comprises a sequence comprising adenosine-thymidine repeats $(AT)_n$ ($n \geq 2$) in each strand. In some embodiments, $n \geq 2$, 3, 4, 5, 6, 7, 8, 9, 10, 11, 12, 13, 14, 15, 16, 17, 18, 19, 20, 21, 22, 23, 24, 25, 26, 27, 28, 29, 30, 34, 32, 33, 34, 35, 36, 37, 38, 39, 40, 41, 42, 43, 44, 45, 46, 47, 48, 49, or 50. In a specific embodiment, in the sc state, the sequence comprising (AT)n adopts, for example, the hairpin/cruciform structures in each strands of the circular double-stranded plasmid, while in the rx circular dsDNA molecule, the sequences comprising (AT)n are in a double-stranded conformation.

In one embodiment, the circular double-stranded plasmid may comprise at least 4-base pair ATs, at least 6-base pair ATs, at least 8-base pair ATs, at least 10-base pair ATs, at least 12-base pair ATs, at least 14-base pair ATs, at least 16-base pair ATs, at least 18-base pair ATs, at least 20-base pair ATs, at least 22-base pair ATs, at least 24-base pair ATs, at least 26-base pair ATs, at least 28-base pair ATs, at least 30-base pair ATs, at least 32-base pair ATs, at least 32-base pair ATs, at least 34-base pair ATs, at least 36-base pair ATs, at least 38-base pair ATs, at least 40-base pair ATs, or at least 42-base pair ATs.

In some embodiments, the (AT), sequence in a single strand of the instant ds DNA molecule may comprise a minimal of about 10 AT dinucleotides to a maximal of about 80 AT dinucleotides. For example, the instant dsDNA molecule can comprise AT dinucleotide sequences from about 10 ATs to about 70 ATs; about 10 ATs to about 60 ATs; about 10 ATs to about 50 ATs; about 10 ATs to about 40 ATs; 15 ATs to about 30 ATs; about 18 ATs to about 25 ATs; or about 20 to about 25 ATs.

In one embodiment, the circular double-stranded plasmid comprises at least one DNA endonuclease or exonuclease recognition site that can be recognized by a DNA endonuclease or exonuclease. Subsequently, the circular double-strand plasmid is cleaved or digested by such endonuclease or exonuclease, failing to maintain relaxed and supercoiled configurations.

In a specific embodiment, the circular double-stranded plasmid is pAB1. Plasmid pAB1 (SEQ ID NOs: 1-2) is a double-stranded circular DNA molecule that contains 2757 base pairs. It can be propagated in *E. coli* cells, such as DH5a, and Top10. It comprises a 42-base pair AT sequence that can form two hairpin structures when pAB1 becomes negatively supercoiled, i.e., one hairpin structure in each strand.

In one embodiment, the assays and methods of the subject invention take advantage of a unique property of T5E that can initiate nucleotide removal from the 5' termini or at gaps and nicks of linear or circular dsDNA in the 5' to 3' direction. While T5E does not degrade sc dsDNAs and relaxed (rx) DNAs, e.g., rx plasmid pAB1, it can digest sc dsDNAs, e.g., sc plasmid pAB1, that carries a hairpin structure or contains linear and nicked DNA. After the T5E digestion, the DNA samples can be stained by a DNA-binding dye, e.g., either DNA intercalators or groove binders, to differentiate relaxed and supercoiled DNA.

The instant circular plasmids comprising one or more hairpin structures upon supercoiling can be used to screen or identify inhibitors of enzymes that regulate DNA topology, e.g., DNA topoisomerases. For example, to determine the presence of an inhibitor of a DNA topoisomerase, a sample suspected of containing an inhibitor of the DNA topoisomerase is added to a mixture of the DNA topoisomerase and a circular plasmid comprising one or more hairpin structures upon supercoiling. After adding the T5E, the sc circular plasmid is digested into small fragments while the rx circular plasmid maintains its conformation, which can bind to a DNA-staining dye. The fluorescence intensity from the relaxed DNA samples is significantly higher than that of supercoiled DNA samples.

Specifically, in the presence of a DNA topoisomerase I, the supercoiled circular dsDNA molecules comprising two hairpin structures undergo relaxation so that T5E cannot digest such circular dsDNA. Such relaxed circular dsDNA, thus, can bind to the DNA-staining dye, resulting in an increase in the fluorescence. In the presence of an inhibitor of the DNA topoisomerase I, T5E digests the sc circular DNA molecules comprising two hairpin structures into small DNA fragments, leading to no or little fluorescence in the presence of the DNA-staining dye.

For example, in the presence of a DNA gyrase, the circular dsDNA molecule undergoes supercoiling, forming, e.g., two hairpin structures. T5E digests such sc circular dsDNA molecule into small DNA fragments, which produce little or no fluorescence in the presence of a DNA-staining dye. In the presence of an inhibitor of the DNA gyrase, the circular dsDNA molecule fails to undergo supercoiling and remain in the rx configuration, which cannot be digested by T5E. The rx circular dsDNA molecule can then bind to a DNA-staining dye and produce a fluorescence that is significantly higher than when the DNA gyrase is not inhibited.

In one embodiment, the subject invention provides a method for screening/identifying inhibitors targeting an enzyme that regulates the DNA topology, e.g., DNA topoisomerase, the method comprises providing a sample suspected of containing an inhibitor of the enzyme, e.g., DNA topoisomerase; mixing the enzyme, e.g., DNA topoisomerase, and a circular dsDNA molecule with the sample, wherein the circular dsDNA molecule comprises one or more hairpin structures in each strand upon supercoiling; adding an exonuclease, e.g., T5E, or an endonuclease into the mixture, wherein the exonuclease/endonuclease, e.g., T5E, digests the circular dsDNA molecule in a sc configuration comprising one or more hairpin structures in each strand into small fragments; adding a signal reporter, e.g., a DNA-staining dye; and determining the presence or absence of the inhibitor based on a signal generated from the signal reporter, e.g., fluorescence, in the sample, wherein the signal reporter reacts only to the small nucleic acid fragments or the nucleic acid molecule in a relaxed configuration.

In one embodiment, the method may further comprise determining and/or quantifying the signal from the reporter in the sample mixture. The signal can be determined or quantified through, for example, an optical measurement, e.g., fluorescent or luminescent detection, colorimetry, and light scatter (turbidity).

In one embodiment, the subject invention provides a method for determining the presence of an inhibitor targeting a DNA topoisomerase in a sample, the method comprising providing the sample suspected of containing an inhibitor of a DNA topoisomerase; adding a circular double-stranded plasmid comprising an adenosine-thymidine dinucleotide repeat (AT)n sequence, wherein n≥2, in each strand, wherein the (AT)n sequence forms a hairpin structure upon supercoiling of the circular double-stranded plasmid; adding the DNA topoisomerase; adding T5E; adding a DNA-staining dye; and determining the presence or absence of the inhibitor based on the fluorescence in the sample.

In a specific embodiment, the circular double-stranded plasmid comprising an adenosine-thymidine dinucleotide repeat (AT)n sequence in each strand does not comprise any label (e.g., fluorescent dye).

In one embodiment, the subject invention provides a method for screening/identifying inhibitors targeting a DNA topoisomerase I, the method comprising: providing in a sample suspected of containing an inhibitor of the DNA topoisomerase I; adding a circular double-stranded plasmid, wherein the circular double-stranded plasmid is in a sc configuration comprising two hairpin structures; adding the DNA topoisomerase I; adding T5E; adding a DNA-staining dye; and determining the presence or absence of the inhibitor based on the fluorescence of the sample.

In one embodiment, the method further comprises quantifying the amount of inhibitor present in the sample based on the fluorescence measured in the sample compared to the fluorescence measured in a control sample containing a DNA topoisomerase I, and the circular double-stranded plasmid, wherein the fluorescence in the control sample is high due to the interconversion of the circular double-stranded plasmid to a relaxed conformation in the presence of the DNA topoisomerase; and the fluorescence in the sample is lower than in the control sample if the sample contains an inhibitor of the DNA topoisomerase I.

In a specific embodiment, the circular double-stranded plasmid comprising an (AT)n sequence forming the hairpin structure in each strand. In a further embodiment, the two hairpin structures may have an identical or different length.

In one embodiment, the subject invention provides a method for screening/identifying inhibitors targeting DNA gyrase, the method comprising: providing a sample suspected of containing an inhibitor of DNA gyrase; adding a circular double-stranded plasmid, wherein the circular double-stranded plasmid is in a relaxed configuration; adding the DNA gyrase; adding T5E; adding a DNA-staining dye; and determining the presence or absence of the inhibitor based on fluorescence in the sample, wherein a strong fluorescence in the sample is indicative of the inhibition of DNA gyrase by the inhibitor while a low or no fluorescence is indicative of the absence of the inhibitor.

In one embodiment, the method further comprises quantifying the amount of inhibitor of DNA gyrase present in the sample based on the fluorescence measured in the sample compared to the fluorescence measured in a control sample containing a DNA gyrase, and the circular double-stranded plasmid; wherein the fluorescence in the control sample is low due to the interconversion of the circular double-stranded plasmid to a sc conformation in the presence of the DNA gyrase; and the fluorescence in the sample is higher than in the control sample.

In one embodiment, the sample is suspected of containing an inhibitor of a DNA topoisomerase e.g., bacterial or human DNA topoisomerase I or DNA gyrase. In a specific embodiment, the sample suspected of containing an inhibitor of a DNA topoisomerase comprises a library of compounds that potentially target DNA topoisomerases.

In certain embodiments, the T5E is added in the sample at an amount that can completely digest the sc circular dsDNA molecule of the subject invention. For example, T5E is added in the sample at a final concentration of 10 nM to 1 mM, 10 nM to 0.5 mM, 10 nM to 0.2 mM, 10 nM to 0.1 mM, 20 nM to 0.1 mM, 50 nM to 0.1 mM, 100 nM to 0.1 mM, 150 nM to 50 µM, 100 nM to 50 µM, 100 nM to 20 µM, 100 nM to 10 µM, 100 nM to 5 µM, 150 nM to 10 µM, 150 nM to 5 µM, 150 nM to 2 µM, 150 nM to 1 µM, 150 nM to 750 nM, or 150 nM to 500 nM.

In one embodiment, the DNA dyes that can be used in the subject invention include, but are not limited to, Hoechst 33258, SYBR gold, ethidium bromide, EthD-1, and SYBR green. Preferably, the dye is ethidium bromide, or EthD-1.

In one embodiment, the method further comprises a step of incubating the T5E in the sample prior to adding the DNA-staining dye and determining/quantifying the fluorescence of the sample. In some embodiments, the T5E is incubated with the sample for at least 5 minutes, 10 minutes, 15 minutes, 20 minutes, 25 minutes, 30 minutes, 45 minutes, 60 minutes, 90 minutes, or 120 minutes. In certain embodiments, the T5E is incubated with the sample for about 5 minutes to 5 hours, about 15 minutes to 4 hours, about 30 minutes to 3 hours, about 45 minutes to 2.5 hours, or about 1 to 2 hours.

In one embodiment, the method of the subject invention also comprises adding a nucleoside triphosphate in the sample. In a specific embodiment, the nucleoside triphosphate is ATP. In specific embodiments, the nucleoside triphosphate may be added at a maximal concentration of 12 mM, 10 mM, 9 mM, 8 mM, 7 mM, 6 mM, or 5 mM. In some embodiments, the nucleoside triphosphate may be added at a concentration of 0.01 mM to 10 mM, 0.1 mM to 10 mM, 0.5 mM to 10 mM, 1 mM to 10 mM, 2 mM to 10 mM, 3 mM to 10 mM, 4 mM to 10 mM, 5 mM to 10 mM, 1 mM to 5 mM, or 2 mM to 5 mM.

In one embodiment, the subject invention provides a method for determining, screening or identifying inhibitors of one or more DNA topoisomerase in a sample, the method consisting of providing a sample suspected of containing an inhibitor of a DNA topoisomerase; adding a circular double-stranded plasmid of the subject invention; adding the DNA topoisomerase; adding ATP to the sample; adding a T5 exonuclease (T5E) and incubating, preferably, for at least 1 hour; adding a DNA-staining dye; and determining the presence or absence of the inhibitor based on the fluorescence in the sample.

In one embodiment, methods known in the art may be used for quantifying the fluorescence in the sample. Such methods include, for example, fluorescence microscopy and plate readers.

Among the DNA topoisomerases that can be detected using the instant nucleic acid molecules, assays and methods include, but are not limited to, type I DNA topoisomerases: type IA and type IB DNA topoisomerases and type II DNA topoisomerases: type IIA and type IIB DNA topoisomerases. The following are some examples of DNA topoisomerases:

bacterial topoisomerases, including E. coli topoisomerase I, III, and IV, Mtb DNA topoisomerase I (MtbTopoI); bacterial DNA gyrase, e.g., E. coli DNA gyrase or Mtb DNA gyrase; virus topoisomerase, e.g., Variola topo I; human topoisomerases I and IIa and other topoisomerase IA and IB topoisomerases, and other topoisomerase IIA and IIB topoisomerases. The methods can also be used to screen for yeast topoisomerase II, mammalian topoisomerase II e.g., IIa and IIb, prokakryotic DNA topoisomerase III, yeast DNA topoisomerase III, mammalian DNA topoisomerase IIIa and IIIb, and poxvirus and vaccinia DNA topoisomerases.

In certain embodiments, the DNA topoisomerase is selected from DNA topoisomerase I, II, III, IV, V and DNA gyrase. In a specific embodiment, the DNA topoisomerase is bacterial DNA topoisomerase I, bacterial DNA gyrase, human DNA topoisomerase I or human DNA topoisomerase II. In a preferred embodiment, the DNA topoisomerase I is E. coli topoisomerase I, Variola topoisomerase I, Mtb topoisomerase I or human DNA topoisomerase I.

In one embodiment, the subject invention provides a method for determining the potency of an inhibitor of DNA topoisomerases including topoisomerase I and DNA gyrase, by evaluating the IC50 of the inhibitor. The method may comprise adding a series of concentrations of the inhibitor in the sample comprising DNA topoisomerases with the circular double-stranded plasmid of the subject invention; adding T5E; adding a DNA-staining dye; quantifying the fluorescence of the sample; and determining the IC50 of the inhibitor.

In one embodiment, the method of the subject invention can also be used to screen potential compounds as antibacterial and/or anticancer drugs. In certain embodiments, the compounds that target DNA topoisomerases, or DNA gyrases may have activity against E. coli, Staphylococcus aureus, Streptococcus pneumoniae, Helicobacter pylori, Mycobacterium bovis, Mycobacterium africanum, Mycobacterium microti, Mycobacterium canetti, M. smegmatis and/or M. tuberculosis.

In one embodiment, the subject invention also provides a method for screen/identifying DNA intercalators, the method comprising, or consisting of, providing a sample suspected of containing a DNA intercalator; adding a circular double-stranded plasmid of the subject invention, the circular double-stranded plasmid being in a supercoiled configuration and comprising one or more hairpin structures in each strand; adding T5E; adding a DNA-staining dye; and determining the presence or absence of the DNA intercalator based on the fluorescence in the sample, wherein a higher fluorescence in the sample than a control is indicative of the presence of the DNA intercalator, wherein the control may comprise the circular sc double-stranded plasmid in the absence of a DNA intercalator.

DNA intercalators are molecules capable of fitting between nucleic acid base pairs. DNA intercalators can inhibit DNA replication in rapidly growing cancer cells. Thus, the method of the subject invention may be used for screening or identifying new drugs for treating cancers.

The subject invention provides circular dsDNA molecules, assays and methods that can be used for rapid and efficient HTS, for example, in a 96-well, 384-well or 1536-well plates setting, to identify potential inhibitors from various compound libraries. Advantageously, only a small amount, e.g., a few nanograms, of the nucleic acid molecules and T5E are needed for each reaction.

High-throughput screening methods can leverage robotics and automation to quickly test the biological or biochemical activity of a large number of molecules, e.g., drugs. Large scale compound libraries can quickly be screened in a cost-effective way to accelerate target analysis and assess pharmacologically profiling agonists and antagonists for receptors and enzymes.

In specific embodiments, the subject invention provides methods for HTS to identify inhibitors of one or more enzymes that affects the DNA topology, the method comprising providing a sample carrier, e.g., HTS plates such as microplate, comprising arrays of individual reservoir, each reservoir containing a compound of a screening library or a control, adding a circular dsDNA molecule of the subject invention and an enzyme in each reservoir; adding an exonuclease, e.g., T5E, or an endonuclease in each reservoir; adding a DNA-staining dye; determining the inhibitors of one or more enzymes based on the fluorescence in each reservoir.

In one embodiment, the method of the subject invention can be used for determining the presence of inhibitors targeting a DNA topoisomerase in a sample. In one embodiment, the method of the subject invention can also be used for screening or identifying inhibitors of DNA endonuclease, and DNA nicking endonuclease.

In one embodiment, the circular double-stranded DNA molecules of the subject invention can be used to detect and quantify the presence of DNA topology affecting enzymes such as DNA topoisomerases, DNA gyrases, DNA nicking endonucleases, and DNA endonucleases, in a biological sample, for example, via the methods of the subject invention.

In one embodiment, the subject invention also provides kits for screening inhibitors of DNA topoisomerases, e.g., topoisomerase I and DNA gyrase. The kit can comprise, for example, a circular double-stranded DNA plasmid of the subject invention, a DNA topoisomerase, a DNA-staining dye and T5E, wherein the circular ds plasmid is in the supercoiled or relaxed conformation and the kit can be used to detect inhibitors of the DNA topoisomerases.

The kits may further be used in the methods described herein. The kits may also include at least one reagent and/or instructions for their use. Also, the kits may include one or more containers filled with reagent(s), and/or one or more molecules for use according to the invention. The kits may also comprise a control composition, nucleoside triphosphates and/or buffers. In a specific embodiment, the control composition may comprise novobiocin and/or ciprofloxacin.

In certain embodiments, the kits may additionally include reagents and means for detecting the labels provided on the molecules used according to the invention. As it would be understood by those skilled in the art, additional detection or labeling methodologies may be used in the kits provided.

As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," and "comprise" can be used interchangeably; "consisting essentially of," and "consists essentially of" can be used interchangeably; and "consisting," and "consists" can be used interchangeably.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

When ranges are used herein, such as for dose ranges, combinations and subcombinations of ranges (e.g., subranges within the disclosed range), specific embodiments therein are intended to be explicitly included.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Where particular values are described in the application and claims, unless otherwise stated the term "about" meaning within an acceptable error range for the particular value should be assumed.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

The present invention is further illustrated by the following examples that should not be construed as limiting. The contents of all references, patents, and published patent applications cited throughout this application, as well as the Figures, are incorporated herein by reference in their entirety for all purposes.

EXAMPLES

Materials and Methods

*E. coli* DNA topoisomerase I was purified according to our previously published procedure (Xu, X. and Leng, F. (2011) A rapid procedure to purify *Escherichia coli* DNA topoisomerase I. *Protein Expr Purif*, 77, 214-9). *E. coli* DNA gyrase subunit A and subunit B were purified as previously described (Wang, Y., Rakela, S., Chambers, J. W., Hua, Z. C., Muller, M. T., Nitiss, J. L., Tse-Dinh, Y. C., & Leng, F. (2019) Kinetic Study of DNA Topoisomerases by Supercoiling-Dependent Fluorescence Quenching. *ACS Omega*. 4, 18413-18422). Mtb DNA topoisomerase I is provided by Prof. Yuk-Ching Tse-Dinh. Variola DNA topoisomerase I was purified as previously described (Wang, Y., Rakela, S., Chambers, J. W., Hua, Z. C., Muller, M. T., Nitiss, J. L., Tse-Dinh, Y. C., & Leng, F. (2019) Kinetic Study of DNA Topoisomerases by Supercoiling-Dependent Fluorescence Quenching. *ACS Omega*. 4, 18413-18422). A Hi-tagged T5 exonuclease was purified from *E. coli* strain BLR(DE3) carrying plasmid pET28a(+)-His-T5E by Ni-NTA column followed by a Q Sepharose Fast Flow column. The His-tag may be removed by TEV protease. Novobiocin and ciprofloxacin were purchased from Sigma-Aldrich, Inc.

The circular ds plasmids can be made in small batches or in large milligram amounts according to standard plasmid purification procedures. Plasmid pAB1 and pAB1_FL905 were described in our published article (Gu, M., Berrido, A., Gonzalez, W. G., Miksovska, J., Chambers, J., and Leng, F. (2016) Fluorescently labeled circular DNA molecules for DNA topology and topoisomerases. Sci Rep. 6:36006). Supercoiled plasmid pAB1 was purified from *E. coli* cells harboring plasmid pAB1 (Top10/pAB1). Relaxed plasmid pAB1 was prepared using variola DNA topoisomerase I or *E. coli* DNA topoisomerase I. Supercoiled pAB1, not relaxed pAB1, can be degraded by certain amount of T5 exonuclease in 1×Cutsmart buffer (NEB; 50 mM Potassium Acetate, 20 mM Tris-acetate, 10 mM Magnesium Acetate, 100 µg/ml BSA pH 7.9@25° C.) or 1×DNA gyrase buffer (35 mM Tris-HCl, pH7.5, 24 mM KCl, 4 mM $MgCl_2$, 2 mM DTT, 0.1 mg/mL BSA, 6.5% glycerol, and 1 mM ATP). Other buffers may also be used. (1% agarose gels are used to determine whether the supercoiled pAB1 was degraded).

For HTS assay to identify inhibitors targeting bacterial DNA topoisomerase I, human DNA topoisomerases and virus (variola) DNA topoisomerase I, supercoiled pAB1 was relaxed in the presence of a chemical compound or potential inhibitor by the DNA topoisomerase I at 37 degrees. Then T5 exonuclease is added into the reaction mixtures and incubated for 2 hours. After this step, EthD1 (a DNA intercalator), or Hoechst33258 (a DNA minor groove binder), or SYBR green (a DNA intercalator) was added, fluorescence intensity was measured by using a plate reader.

Example 1—A Unique Property of T5 Exonuclease

Figure 1A:
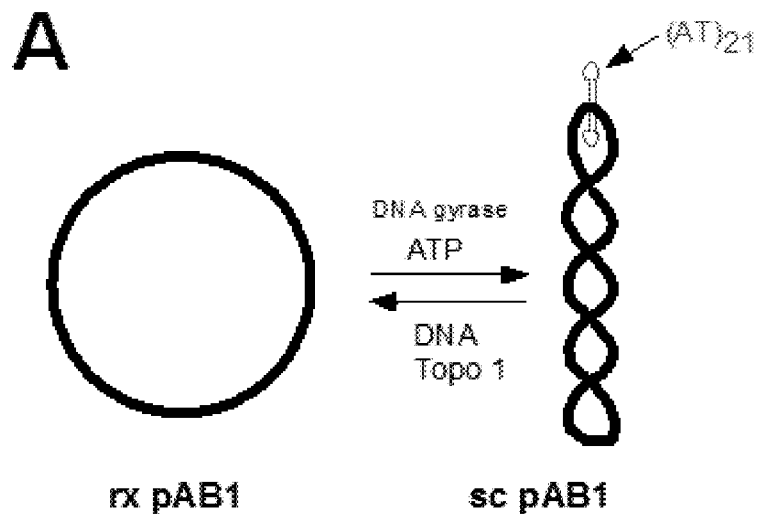
FIGS. 1A-1B show that T5 exonuclease completely digests supercoiled plasmid pAB1 that contains hairpin structures. (A) A hairpin structure is formed from the 42 nt AT sequence when pAB1 becomes negatively supercoiled. (B) T5 exonuclease completely digested sc pAB1 (lanes 1-3) and cannot digest sc plasmid pUC18 (lanes 4-6).
Figure 1B:
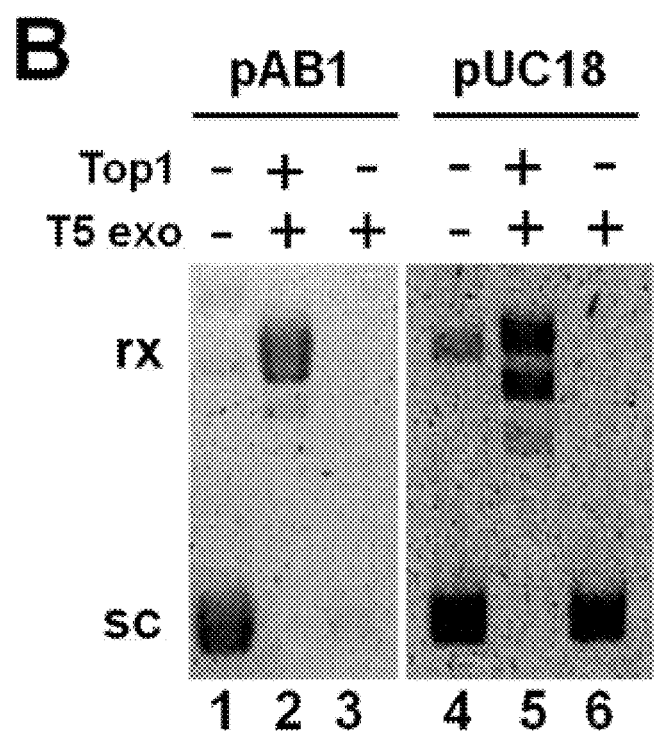

FIG. 1 shows a unique property of T5 exonuclease that completely digested the sc pAB1 carrying a AT hairpin structure (FIG. 1A and lane 3 of FIG. 1B). T5 exonuclease was not able to digest rx pAB1 (lane 2 of FIG. 1B) and rx & sc pUC18. This unique property of T5 exonuclease can be used to configure HTS assays to identify Topo inhibitors.

Example 2—A T5 Nuclease-Based HTS Assay for Bacterial DNA Gyrase

Figure 2A:
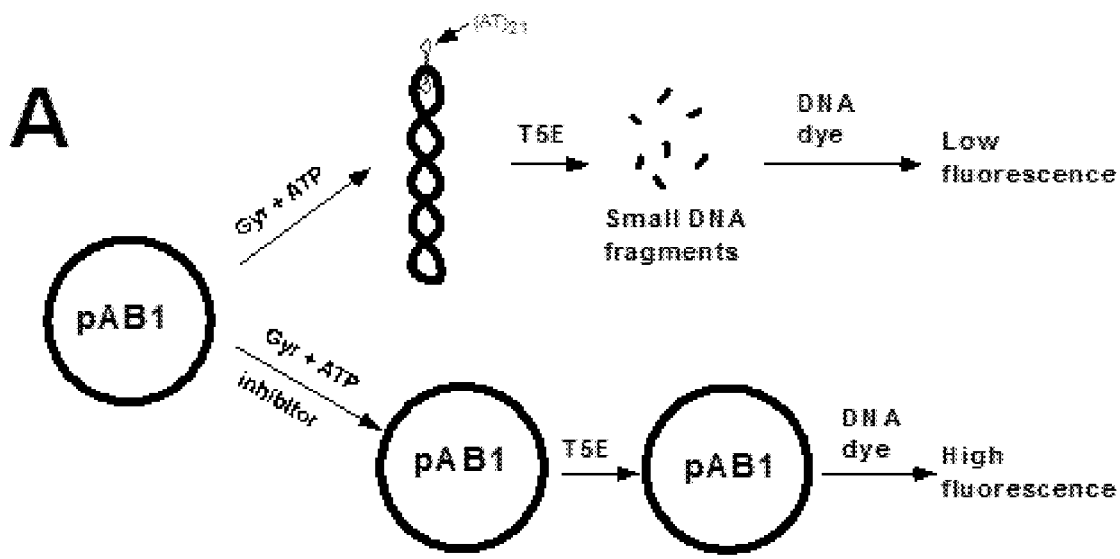
FIGS. 2A-2C show a T5 exonuclease-based assay to identify DNA gyrase inhibitors. (A) An experimental strategy to screen inhibitors targeting bacterial DNA gyrase by T5E. (B) T5E can completely digest sc pAB1 (lanes 2 and 5), but not rx pAB1 (lanes 4 and 6). Novobiocin completely inhibited gyrase activities (lane 6). (C) The DNA-staining dye ethidium homodimer 1 (EthD1) was added to the DNA samples. The fluorescence was measured at $\lambda_{em}$ of 617 nm with $\lambda_{ex}$=528 nm using a plate reader. Lanes 1-6 correspond to the DNA samples of lanes 1-6 in (B), respectively. bk represents background fluorescence in an empty well.
Figure 2B:
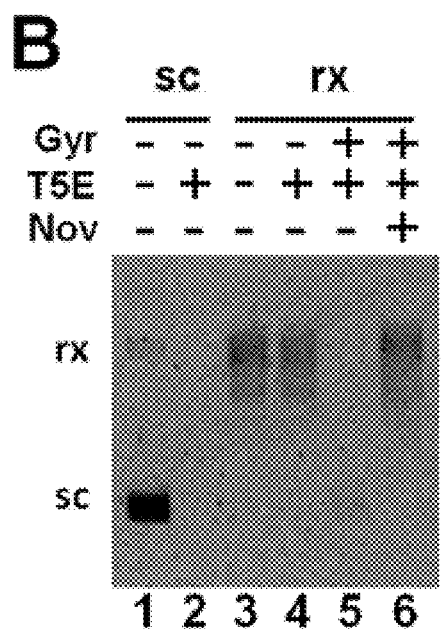

FIG. 2A shows a method to screen/identify inhibitors or other molecules targeting bacterial DNA gyrase. This method can be easily configured into a high throughput format. In the absence of gyrase inhibitors, prokaryotic DNA gyrase can convert the rx DNA templates into the se form. This conversion results in the formation of a hairpin structure in the plasmid. As a result, the sc pAB1 can be completely digested by T5 exonuclease (lane 5 of FIG. 2B). In contrast, gyrase inhibitor novobiocin completely inhibited the bacterial gyrase activities and prevented the conversion of the rx plasmid pAB1 into sc form. T5 exonuclease could not digest rx pAB1 (lane 6 of FIG. 2B).

Figure 2C:
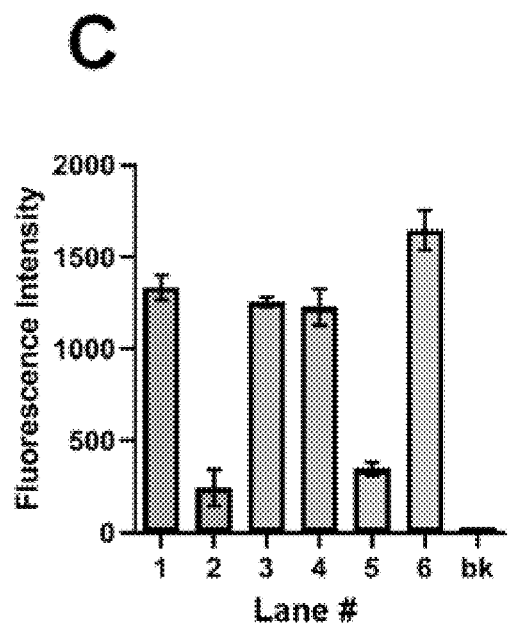
Figure 3A:
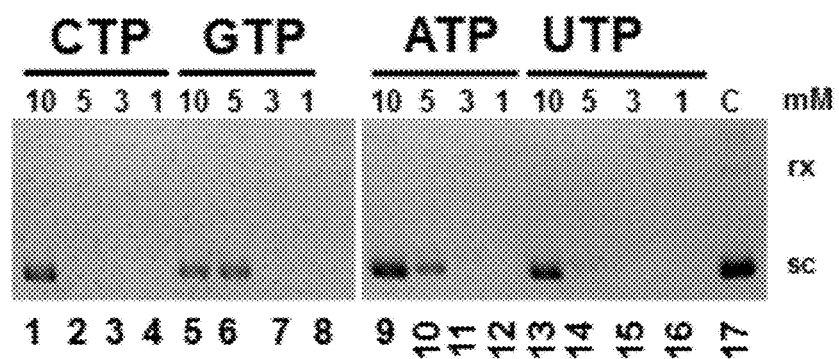
FIGS. 3A-3D show high concentrations of nucleotides inhibit T5 exonuclease activities. (A) Supercoiled plasmid pAB1 was used in the reaction mixtures. C represents the sc pAB1 control sample. Symbols: se, supercoiled; rx, relaxed. (B) A double fluorescently-labeled oligomer HP1 was designed to test the flap endonuclease activities of T5 exonuclease. The 5' and 3'-end of HP1 are labeled with fluorescein (F) and TAMRA (T), respectively. 3'-T and 5'-F represent the TAMRA-labeled and Fluorescein-labeled oligomers digested by T5 exonuclease, respectively. (C) and (D) High concentrations of nucleotides inhibit T5 exonuclease activities using HP1 as the substrate. DNA samples were loaded onto 20% PAGE gels in 1×TAE and photographed. No staining was needed. C represents the HP1 DNA control sample.
Figure 3B:
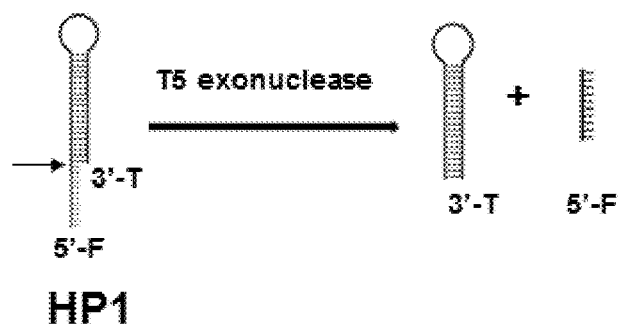
Figure 3C:
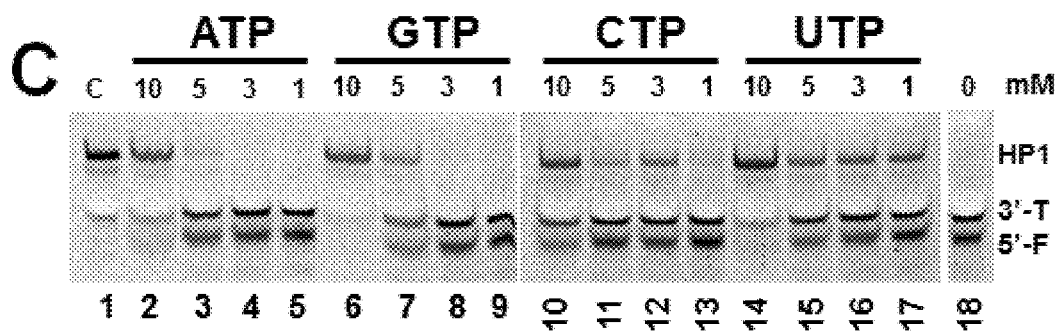
Figure 3D:
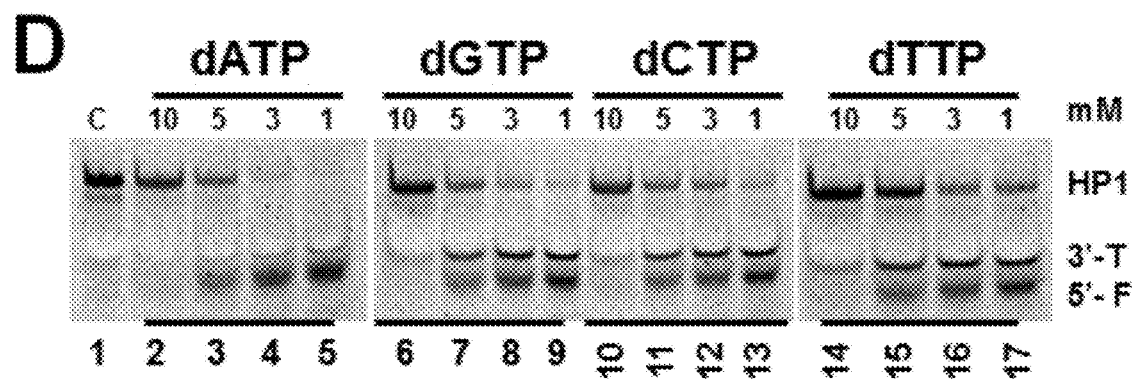

A DNA-staining dye, such as ethidium homodimer 1 (EthD1), can differentiate these two T5 exonuclease-based reactions (FIG. 2C). In the presence of a gyrase inhibitor, the fluorescence intensity of EthD1 is significantly higher comparing with the DNA sample in the absence of a gyrase inhibitor (FIG. 2C). High concentrations of ATP could inhibit T5 exonuclease activities and may interfere with this assay (FIG. 3).

Figure 4A:
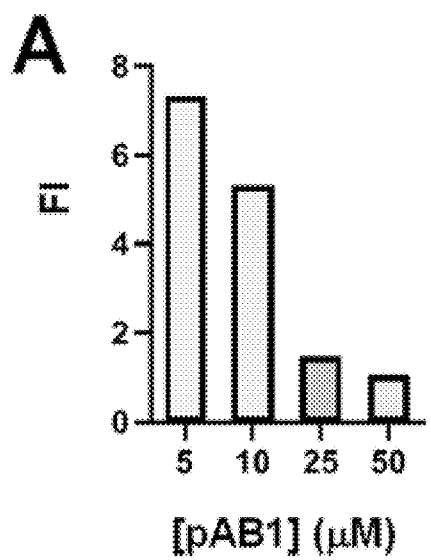
FIGS. 4A-4E show the determination of the optimal conditions for the T5 exonuclease based HTS assay to screen and identifying bacterial DNA gyrase inhibitors. The T5 nuclease-based HTS assay for bacterial DNA gyrase is described under Method and FIG. 2A. The fluorescence was measured at $\lambda_{em}$ of 617 nm with $\lambda_{ex}$=528 nm using a plate reader. (A-C) The plasmid pAB1 DNA concentration, T5 exonuclease concentration, and E. coli DNA gyrase concentration were varied, respectively. (D and E) The T5 exonuclease time was changed for the assay.
Figure 4B:
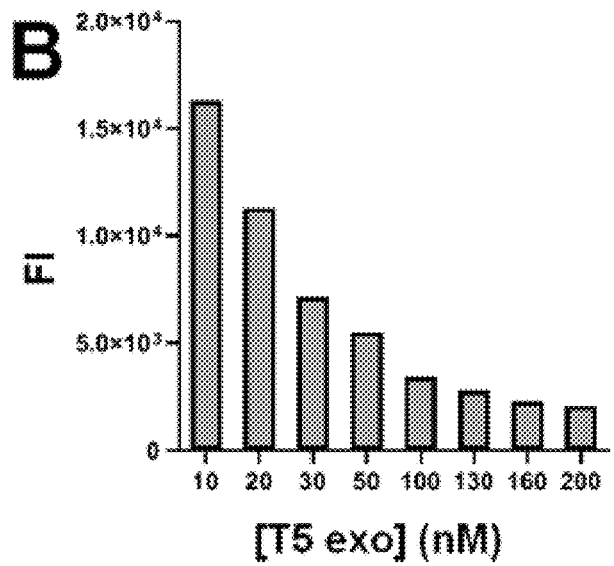
Figure 4C:
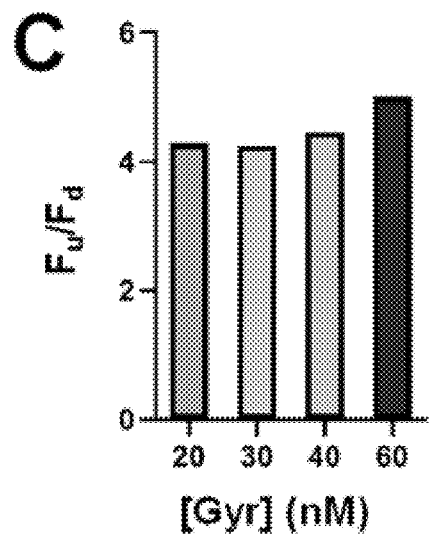
Figure 4D:
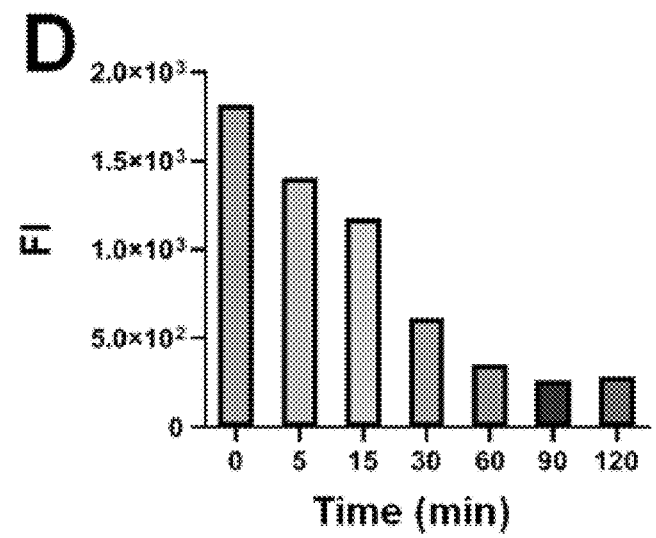
Figure 4E:
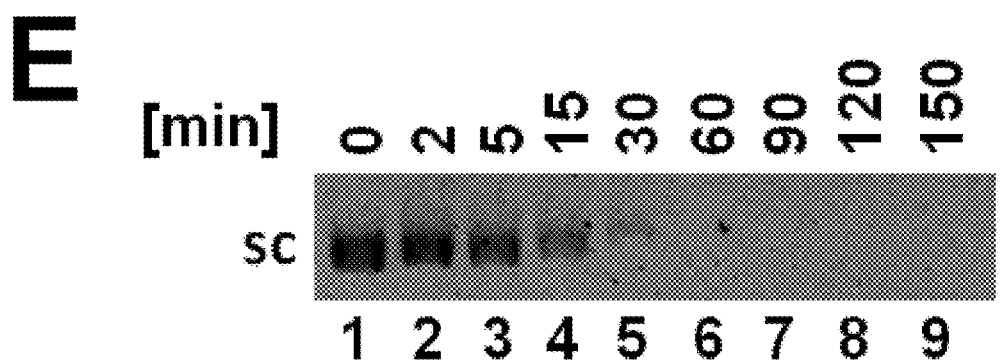

A series of experiments were performed to determine the optimal conditions for the T5 exonuclease based assay for *E. coli* DNA gyrase (FIGS. 4A-E). After these experiments, 10

μM (bp) of pAB1 (FIG. 4A), 200 nM of T5 exonuclease (FIG. 4B) and 20 nM of *E. coli* DNA gyrase (FIG. 4C) were chosen for the assay. The assay tolerated up to 2% DMSO without any significant change in signal. Additionally, 1-2 hours of incubation with T5 exonuclease may be needed for the assay (FIGS. 4D and E).

Several different DNA-staining dyes, i.e., hoechst33258, SYBR green, SYBR gold, ethidium bromide, and EthD1 with different fluorescence excitation and emission wavelengths were examined (FIG. 5). All can be used in the assay depending on the fluorescence interference that the potential gyrase inhibitors have.

Figure 5A:
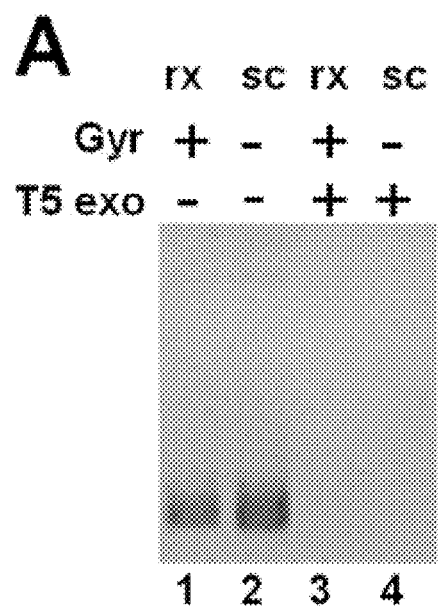
Figure 5B:
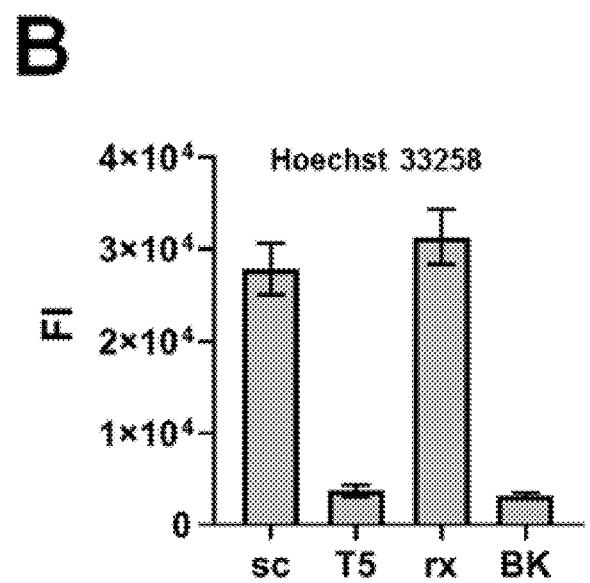
Figure 5C:
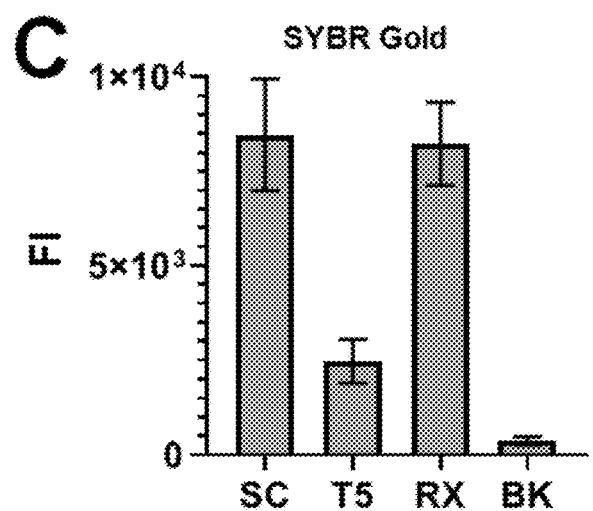
Figure 5D:
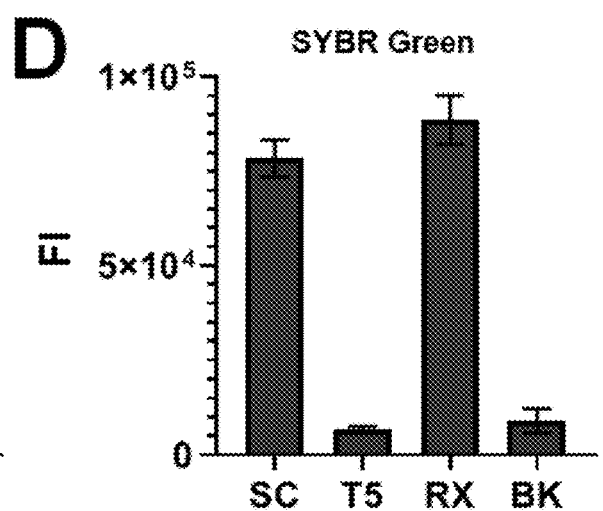
Figure 5E:
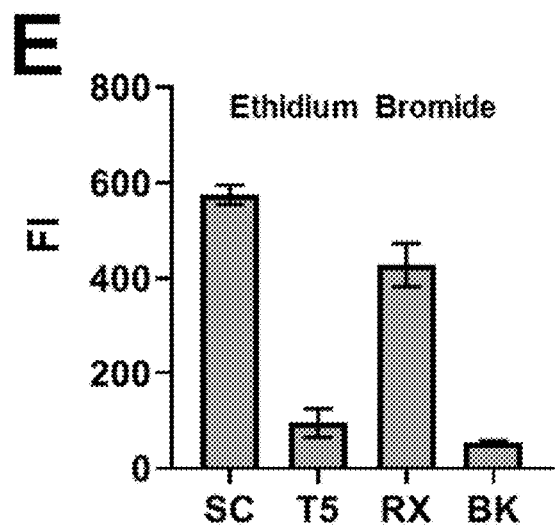
Figure 5F:
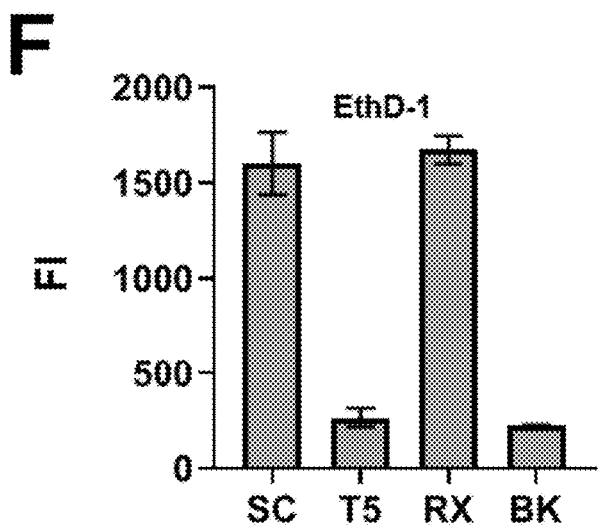

Hoechst 33258 gives the highest fluorescence difference of the DNA samples in the presence and absence of T5 exonuclease (FIGS. 5A and B). EDH1 was chosen for use for the following HTS assays because this DNA-binding dye tightly binds to DNA and has good fluorescence signals upon DNA binding. Ethidium bromide is inexpensive and can be used as well (FIG. 5E).

Titration experiments were performed, in which different concentrations of novobiocin and ciprofloxacin were added into the assays. FIG. 6 shows that ciprofloxacin and novobiocin potently inhibited the activities of DNA gyrase with an estimated IC50 of 3.1 and 0.48 μM, respectively.

Example 3—Screening of *E. coli* Gyrase Inhibitors by T5 Exonuclease-Based HTS Assay A 50-compound library that contains 9 known bacterial DNA gyrase inhibitors was assembled (Table 1) in order to establish and validate the T5 exonuclease based HTS assay for *E. coli* DNA gyrase. The compounds were added in the screening plate as indicated in Table 1.

TABLE 1

50-compound library

| HTS Plate | Name | Structure | CID | NSC |
|---|---|---|---|---|
| 1A | Novobiocin | 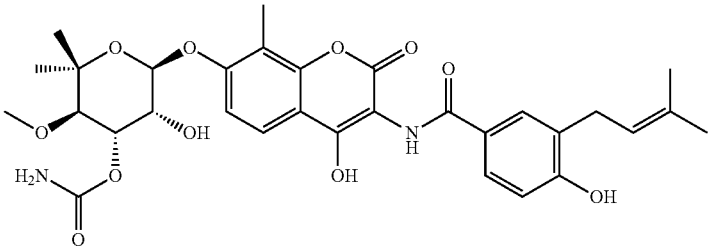 | 54675769 | |
| 1B | Levofloxacin | 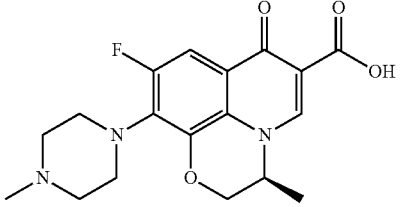 [SMILES: C[C@H]1COc2c(N3CCN(C)CC3)c(F)cc3c(=O)c(C(=O)O)cn1c23] | 149096 | 758709 |
| 1C | Ciprofloxacin | 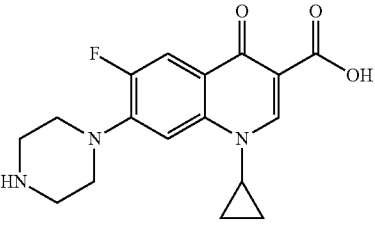 [SMILES: O=C(O)c1cn(C2CC2)c2cc(N3CCNCC3)c(F)cc2c1=O] | 2764 | 758467 |
| 1D | Oxolinic acid | 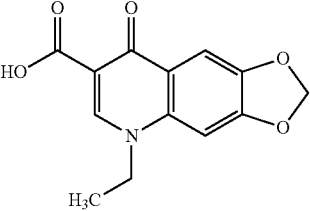 [SMILES: CCn1cc(C(=O)O)c(=O)c2cc3c(cc21)OCO3] | 4628 | 758177 |

TABLE 1-continued 50-compound library

| HTS Plate | Name | Structure | CID | NSC |
|---|---|---|---|---|
| 1E | Enrofloxacin | | 71188 | 758616 |
| 1F | Norfloxacin | 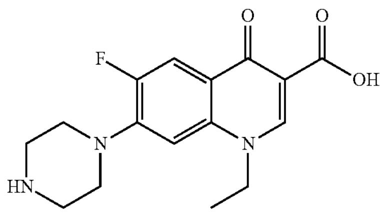 [SMILES: CCn1cc(C(=O)O)c(=O)c2cc(F)c(N3CCNCC3)cc21] | 4539 | 757250 |
| 1G | Nalidixic acid | 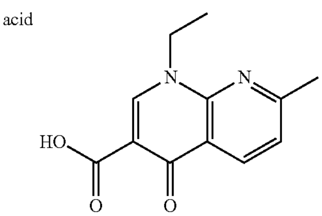 | 4421 | 757432/ 82174 |
| 1H | Lomefloxacin | 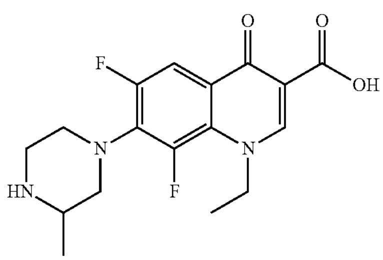 [SMILES: CCn1cc(C(=O)O)c(=O)c2cc(F)c(N3CCNC(C)C3)c(F)c21] | 3948 | |
| 2A | suramin | 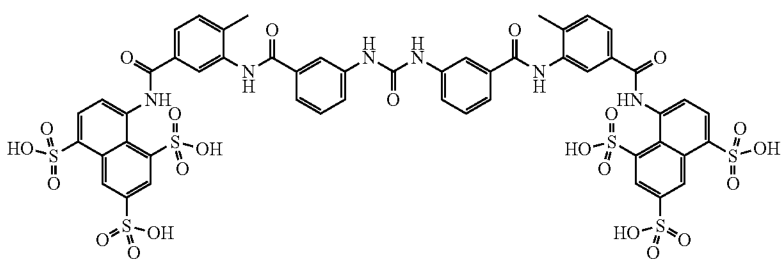 [SMILES: Cc1ccc(C(=O)Nc2ccc(S(=O)(=O)O)c3cc(S(=O)(=O)O)cc(S(=O)(=O)O)c23)cc1NC(=O)c1cccc(NC(=O)Nc2cccc(C(=O)Nc3cc(C(=O)Nc4ccc(S(=O)(=O)O)c5cc(S(=O)(=O)O)cc(S(=O)(=O)O)c45)ccc3C)c2)c1] | 5361 | 34936 |
| 2B | trovafloxacin | 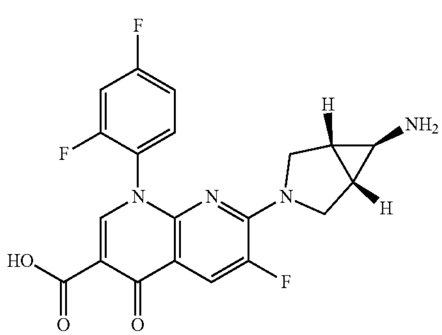 [SMILES: N[C@@H]1[C@H]2CN(c3nc4c(cc3F)c(=O)c(C(=O)O)cn4-c3ccc(F)cc3F)C[C@@H]12] | 62959 | |

TABLE 1-continued
50-compound library
| HTS Plate | Name | Structure | CID | NSC |
|---|---|---|---|---|
| 2C | netropsin | 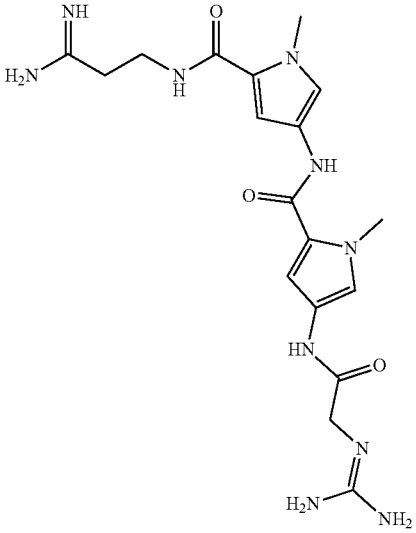 [SMILES: Cn1cc(NC(=O)c2cc(NC(=O)CN=C(N)N)cn2C)cc1C(=O)NCCC(=N)N] | 4461 | |
| 2D | camptothecin | 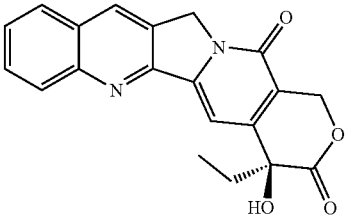 [SMILES: CC[C@@]1(O)C(=O)OCc2c1cc1n(c2=O)Cc2cc3ccccc3nc2-1] | 24360 | 94600 |
| 2E | topotecan | 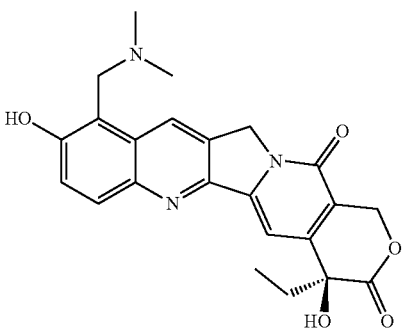 [SMILES: CC[C@@]1(O)C(=O)OCc2c1cc1n(c2=O)Cc2cc3c(CN(C)C)c(O)ccc3nc2-1] | 60700 | 641007 |
| 2F | tyrphostin AG 537 | 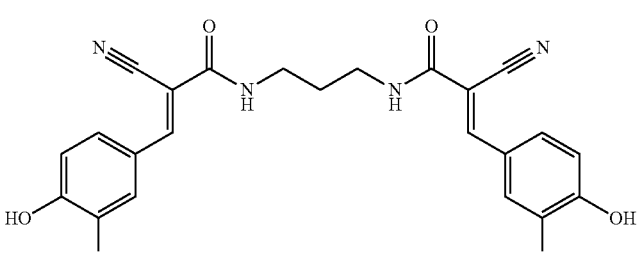 | 5329255 | 676486 |

TABLE 1-continued
50-compound library
| HTS Plate | Name | Structure | CID | NSC |
|---|---|---|---|---|
| 2G | echinomycin | 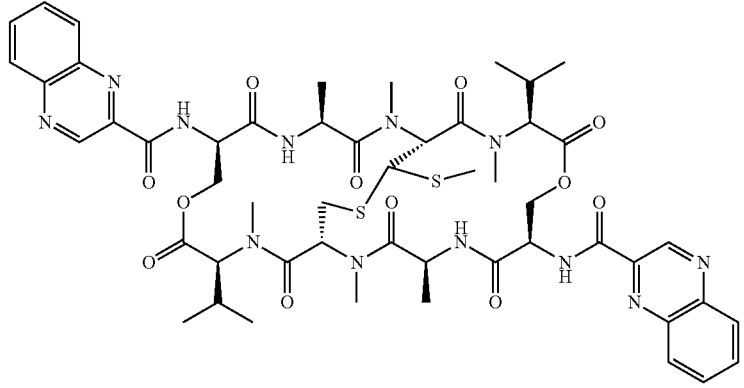 [SMILES: CSC1SC[C@H]2C(=O)N(C)[C@@H](C(C)C)C(=O)OC[C@@H](NC(=O)c3cnc4ccccc4n3)C(=O)N[C@@H](C)C(=O)N(C)[C@@H]1C(=O)N(C)[C@@H](C(C)C)C(=O)OC[C@@H](NC(=O)c1cnc3ccccc3n1)C(=O)N[C@@H](C)C(=O)N2C] | 3197 | 526417/ 13502 |
| 2H | ampicillin | 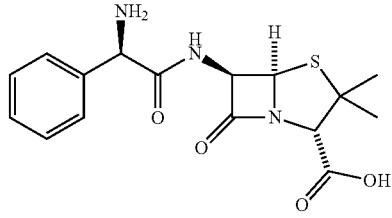 [SMILES: CC1(C)S[C@@H]2[C@H](NC(=O)[C@H](N)c3ccccc3)C(=O)N2[C@H]1C(=O)O] | 6249 | |
| 3A | citrinin | 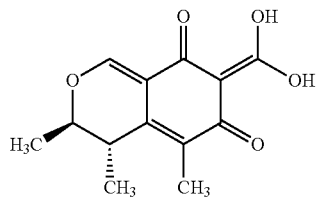 | 54680783 | 186 |
| 3B | Polymyxin B sulfate salt | 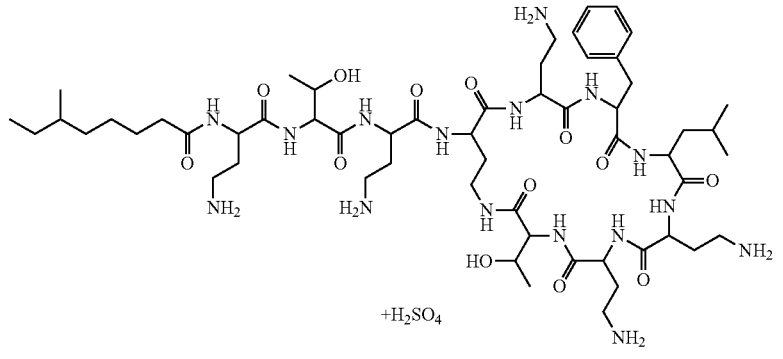 [SMILES: CCC(C)CCCCC(=O)NC(CCN)C(=O)NC(C(=O)NC(CCN)C(=O)NC1CCNC(=O)C(C(C)O)NC(=O)C(CCN)NC(=O)C(CCN)NC(=O)C(CC(C)C)NC(=O)C(Cc2ccccc2)NC(=O)C(CCN)NC1=O)C(C)O ; "+H2SO4"] | 4868 | |
| 3C | L-tryptophan | 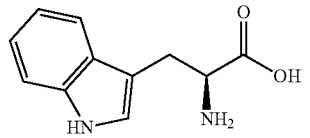 [SMILES: N[C@@H](Cc1c[nH]c2ccccc12)C(=O)O] | 6305 | 757373 |
| 3D | pyridine | 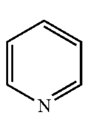 | 1049 | 141574/ 406123 |

TABLE 1-continued 50-compound library

| HTS Plate | Name | Structure | CID | NSC |
|---|---|---|---|---|
| 3E | Spectinomycin | 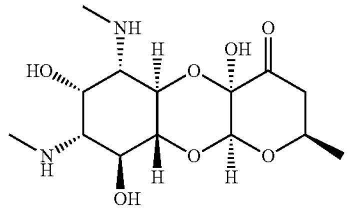 | 15541 | |
| 3F | tetracycline | 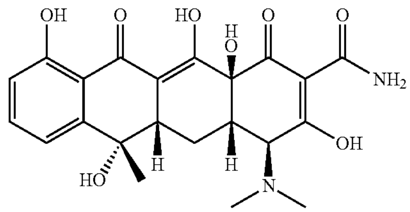 [SMILES: CN(C)[C@@H]1C(O)=C(C(N)=O)C(=O)[C@@]2(O)C(O)=C3C(=O)c4c(O)cccc4[C@@](C)(O)[C@H]3C[C@@H]12] | 54675776 | |
| 3G | sulfanilamide | 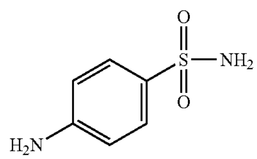 [SMILES: Nc1ccc(S(N)(=O)=O)cc1] | 5333 | 757404/ 7618 |
| 3H | kanamycin | 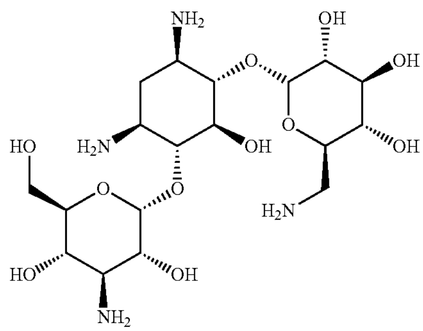 | 6032 | |
| 4A | deoxyadenosine | 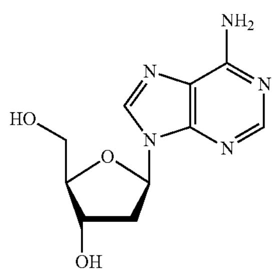 | 13730 | |
| 4B | D-galactose | 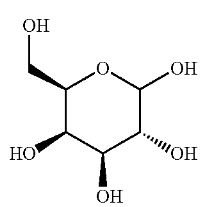 | 6036 | |

TABLE 1-continued
50-compound library
| HTS Plate | Name | Structure | CID | NSC |
|---|---|---|---|---|
| 4C | D-glucose | 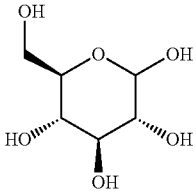 | 5793 | |
| 4D | Glycine | 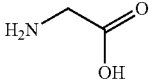 | 750 | 760120/ 25936 |
| 4E | L-arabinose | 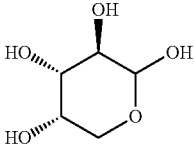 | 439195 | |
| 4F | L-lysine | 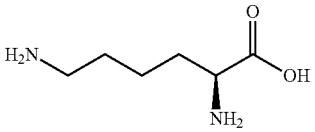 | 5962 | |
| 4G | Vancomycin | 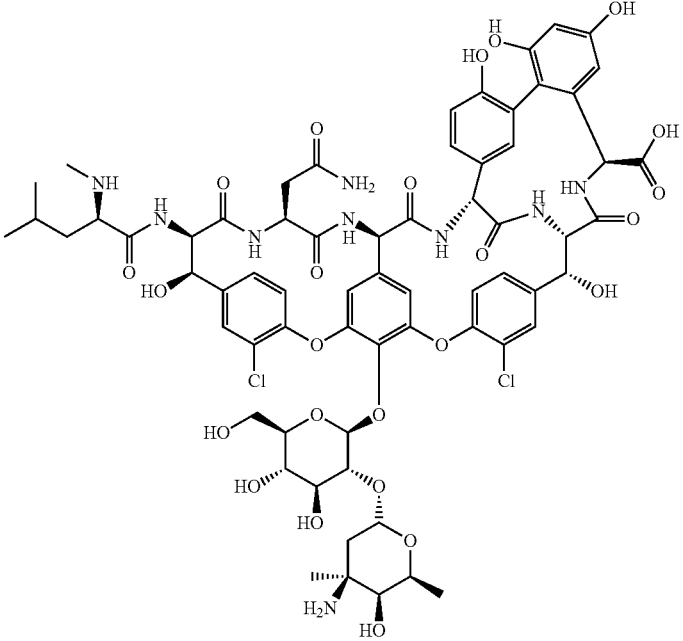 | 14969 | |

TABLE 1-continued
50-compound library
| HTS Plate | Name | Structure | CID | NSC |
|---|---|---|---|---|
| 4H | Bacitracin | 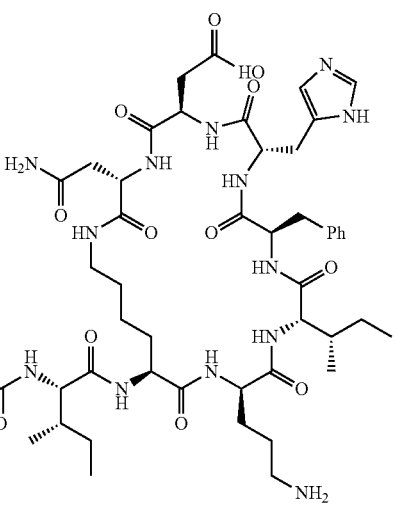 | 11980094 | |
| 5A | ethacridine | 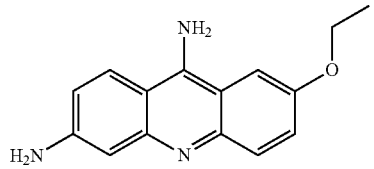 | 2017 | 163296 |
| 5B | Vitamine B1 | 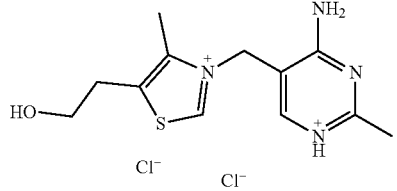 | 135418510 | |
| 5C | imidazole | 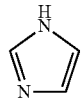 | 795 | 60522 |
| 5D | Chloroquine | 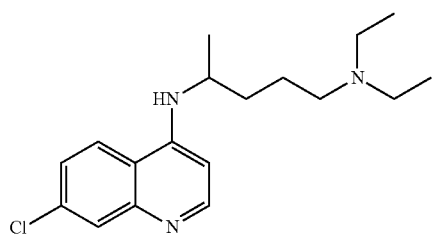 [SMILES: CCN(CC)CCCC(C)Nc1ccnc2cc(Cl)ccc12] | 2719 | 187208 |
| 5E | NSC47384 | 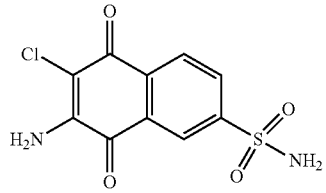 | 240739 | 47384 |

TABLE 1-continued 50-compound library

| HTS Plate | Name | Structure | CID | NSC |
|---|---|---|---|---|
| 5F | NSC54278 | 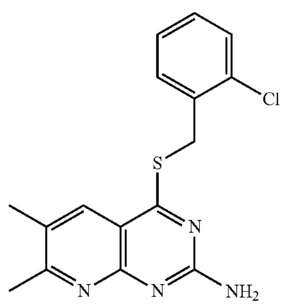 [SMILES: Cc1cc2c(SCc3ccccc3Cl)nc(N)nc2nc1C] | 243964 | 54278 |
| 5G | NSC108753 | 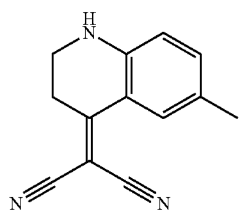 [SMILES: Cc1ccc2c(c1)C(=C(C#N)C#N)CCN2] | 268501 | 108753 |
| 5H | NSC116344 | 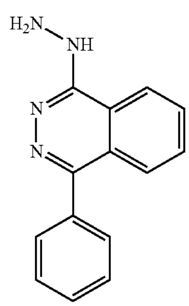 [SMILES: NNc1nnc(-c2ccccc2)c2ccccc12] | 113169 | 116344 |
| 6A | NSC116983 | 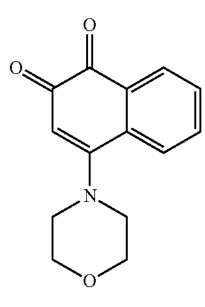 [SMILES: O=C1C=C(N2CCOCC2)c2ccccc2C1=O] | 272529 | 116983 |
| 6B | NSC130785 | 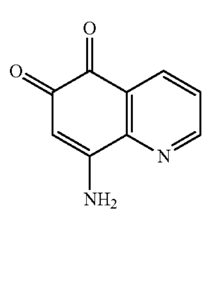 [SMILES: NC1=CC(=O)C(=O)c2cccnc21] | 279596 | 130785 |

TABLE 1-continued
50-compound library
| HTS Plate | Name | Structure | CID | NSC |
|---|---|---|---|---|
| 6C | NSC149044 | 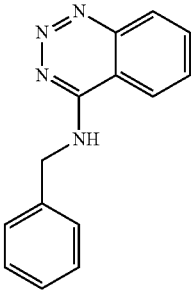 [SMILES: c1ccc(CNc2nnnc3ccccc23)cc1] | 288280 | 149044 |
| 6D | NSC152030 | 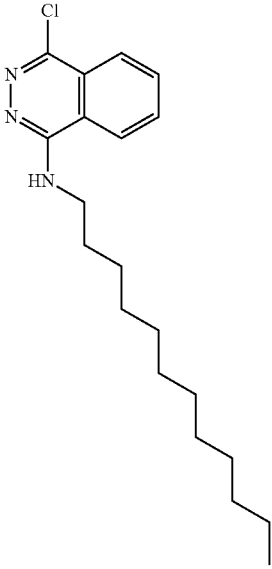 [SMILES: CCCCCCCCCCCCNc1nnc(Cl)c2ccccc12] | 289778 | 152030 |
| 6E | NSC174201 | 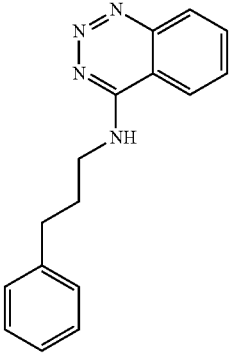 [SMILES: c1ccc(CCCNc2nnnc3ccccc23)cc1] | 300101 | 174201 |
| 6F | NSC409146 | 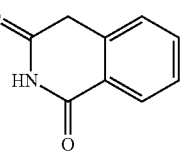 | 349435 | 409146 |

TABLE 1-continued 50-compound library

| HTS Plate | Name | Structure | CID | NSC |
|---|---|---|---|---|
| 6G | NSC601986 | 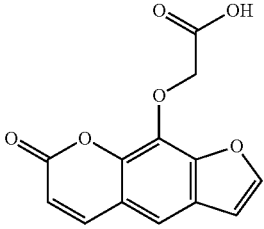 [SMILES: O=C(O)COc1c2occc2cc2ccc(=O)oc12] | 353501 | 601986 |
| 6H | NSC640205 | 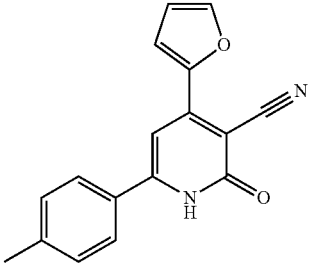 [SMILES: Cc1ccc(-c2cc(-c3ccco3)c(C#N)c(=O)[nH]2)cc1] | 368866 | 640205 |
| 7A | NSC668394 | 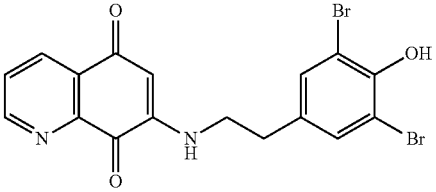 [SMILES: O=C1C=C(NCCc2cc(Br)c(O)c(Br)c2)C(=O)c2ncccc21] | 381594 | 668394 |
| 7B | NSC97419 | 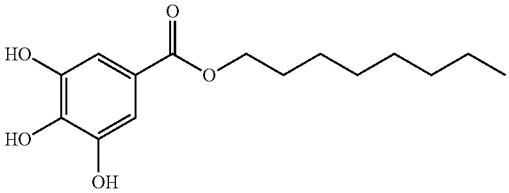 [SMILES: CCCCCCCCOC(=O)c1cc(O)c(O)c(O)c1] | 61253 | 97419 |

The screening results are shown in Table 2. HTS experiments were described in Methods and FIG. 2A. The fluorescence was measured at $\lambda_{em}$ of 617 nm with $\lambda_{ex}$=528 nm using a plate reader. The results (Table 2) indicate that the compounds in 1A (novobiocin), 2A (suramin), 5A (ethacridine), 1B (levofloxacin), 1C (ciprofloxacin), 1BE (enrofloxacin), 1F (norfloxacin), 2G (echinomycin) and 1H (lomefloxacin) are DNA intercalators.

TABLE 2

HTS screening of 50-compound library for *E. coli* DNA gyrase inhibitors.

|   | 1 | 2 | 3 | 4 | 5 | 6 | 7 |
|---|---|---|---|---|---|---|---|
| A | 1688 | 1058 | 527 | 540 | 1407 | 668 | 445 |
| B | 1792 | 643 | 687 | 575 | 467 | 581 | 127 |
| C | 1803 | 478 | 563 | 575 | 496 | 465 |   |
| D | 723 | 570 | 568 | 644 | 672 | 768 |   |
| E | 1884 | 569 | 564 | 562 | 653 | 530 |   |
| F | 1817 | 191 | 588 | 546 | 602 | 539 |   |
| G | 521 | 1775 | 558 | 520 | 698 | 476 |   |
| H | 1689 | 549 | 510 | 579 | 475 | 634 |   |

FIG. 7 shows the results of the screening at 20 μM in triplicate with the following statistics: Z', 0.64, S/B, 4.3, and 9 hits. These 9 hits include novobiocin, 6 fluoroquinolones, suramin, echinomycin, and ethacridine. Suramin is a known DNA topoisomerase II inhibitor. Echinomycin and ethacridine are DNA intercalators and should be able to significantly unwind the plasmid pAB1 at 20 μM. In this case, plasmid pAB1 was fully relaxed or positively supercoiled. The AT hairpin structure was not formed. As a result, T5 exonuclease could not digest the pAB1 DNA samples.

Additionally, pathogen box containing 400 compounds was screened by the new fluorescence-based DNA gyrase assay. After several rounds of screening, two compounds, plate E-07F (CID:MMV688179) and plate E-05A (CID:MMV687798) were found to inhibit *E. coli* DNA gyrase activities. Plate E-05A is a known gyrase inhibitor, Levofloxacin. Plate E-07F is a DNA minor groove binder.

Example 4—Screening of DNA Intercalators by T5 Exonuclease-Based HTS Assay

The T5E-based HTS assay can be used to identify DNA intercalators. In the absence of the DNA intercalator, the sc pAB1 is digested by T5E, which cannot bind to the DNA dye, leading to no or litter fluorescence (FIG. 8). In the presence of the DNA intercalator, the sc pAB1 is converted into the relaxed form, which cannot be digested by T5E. As a result, the rx pAB1 can bind to the DNA dye, leading to a high fluorescence (FIG. 8).

The compounds were added in the screening plate as indicated in Table 1. The screening results are shown in Table 3. The fluorescence was measured at $\lambda_{em}$ of 617 nm with $\lambda_{ex}$=528 nm using a plate reader. The results indicate that the compounds in 5A (ethacridine), and 2G (echinomycin) are DNA intercalators.

TABLE 3

HTS screening of 50-compound library for DNA intercalators.

| | 1 | 2 | 3 | 4 | 5 | 6 | 7 |
|---|---|---|---|---|---|---|---|
| A | 223 | 575 | 230 | 204 | 1367 | 207 | 252 |
| B | 178 | 286 | 191 | 183 | 246 | 249 | 175 |
| C | 202 | 153 | 198 | 207 | 214 | 207 | |
| D | 170 | 259 | 218 | 206 | 220 | 314 | |
| E | 196 | 185 | 220 | 213 | 207 | 226 | |
| F | 173 | 159 | 200 | 217 | 772 | 181 | |
| G | 196 | 1659 | 206 | 187 | 452 | 230 | |
| H | 241 | 304 | 245 | 294 | 193 | 285 | |

Example 5—A T5 Exonuclease-Based HTS Assay for Identifying MtbTopI Inhibitors

FIG. 9 shows a T5 exonuclease based assay to identify MtbTop1 inhibitors. This method can also be easily configured into a high throughput format. In the absence of Mtb topo I inhibitors, the MtbTop1 can convert the sc DNA templates into the rx form, which can not be digested by T5 exonuclease (FIG. 9B). The rx DNA can bind to the DNA dye, e.d., ethidium homodimer 1 (EthD1), leading to a high fluorescence (FIG. 9C). In the presence of the inhibitors of MtbTop1, the sc DNA is digested by T5 exonuclease into small DNA fragments, which results in low fluorescence in the presence of the DNA dye, e.g., EthD1 (FIG. 9C).

The 50-compound library was again used to establish and validate the T5 exonuclease based HTS assay for Mtb topo I. The compounds were added in the screening plate as indicated in Table 1. The screening results are shown in Table 4. The fluorescence was measured at $\lambda_{em}$ of 617 nm with $\lambda_{ex}$=528 nm using a plate reader. The result from suramin, a known inhibitor is shown in 2A. The results from 7A (NSC668394), 7B (NSC97419) and 2E (topotecan) indicate new Mtb DNA topI inhibitors as the result of the screening assay.

TABLE 4

HTS screening of 50-compound library for Mtb DNA topoisomerase 1 inhibitors.

| | 1 | 2 | 3 | 4 | 5 | 6 | 7 |
|---|---|---|---|---|---|---|---|
| A | 1585 | 615 | 1217 | 1455 | 1098 | 1239 | 541 |
| B | 1588 | 1544 | 1730 | 1116 | 1224 | 1082 | 474 |
| C | 1493 | 1444 | 1186 | 1058 | 1372 | 1194 | |
| D | 1515 | 1416 | 1380 | 1321 | 1296 | 1153 | |
| E | 1412 | 716 | 1492 | 1419 | 1276 | 1314 | |
| F | 1192 | 1080 | 1397 | 1246 | 1324 | 1348 | |
| G | 1836 | 1576 | 1523 | 1901 | 1575 | 1379 | |
| H | 1999 | 1353 | 1466 | 1704 | 1486 | 1054 | |

The result shows that the compounds of the library that can inhibit Mtb topo I include Suramin, topotecan, NSC97419, and NSC668394.

Example 6—A T5 Exonuclease-Based HTS Assay for *E. coli* DNA Topoisomerase I

FIG. 10 shows a T5 exonuclease-based assay for identifying *E. coli* DNA topoisomerase 1 inhibitors. In the absence of *E. coli* topo I inhibitors, the *E. coli* Topo I can convert the sc DNA molecule into the rx form, which can not be digested by T5 exonuclease. The rx DNA can then bind to the DNA staining dye, e.g., ethidium homodimer 1 (EthD1), leading to a high fluorescence. In the presence of the inhibitors of *E. coli* Topo I, the sc DNA molecule is digested by T5 exonuclease into small DNA fragments, which results in low fluorescence in the presence of the DNA dye, e.g., EthD1.

The 50-compound library was again used to establish and validate the T5 exonuclease based HTS assay for *E. coli* topo I. The compounds were added in the screening plate as indicated in Table 1. The screening results are shown in Table 5. The fluorescence was measured at $\lambda_{em}$ of 617 nm with $\lambda_{ex}$=528 nm using a plate reader. The number found in 2A indicates the result from suramin, a known inhibitor. The number found in 7A indicates a new *E. coli* DNA Topo I inhibitor, i.e., NSC668394, identified as the result of the screening assay.

TABLE 5

HTS screening of 50-compound library for *E. coli* DNA topoisomerase 1 inhibitors.

| | 1 | 2 | 3 | 4 | 5 | 6 | 7 |
|---|---|---|---|---|---|---|---|
| A | 1071 | 671 | 1384 | 1428 | 1296 | 1791 | 284 |
| B | 1408 | 1998 | 1637 | 1348 | 1441 | 1486 | 949 |
| C | 1191 | 1340 | 1779 | 1703 | 1151 | 1353 | |
| D | 1615 | 2061 | 1339 | 1589 | 1879 | 1642 | |
| E | 2067 | 1730 | 1730 | 1786 | 2083 | 1706 | |
| F | 1817 | 1489 | 1895 | 1914 | 1962 | 1418 | |
| G | 1800 | 1249 | 1426 | 1637 | 1921 | 1667 | |
| H | 1837 | 2034 | 1719 | 2016 | 1610 | 1657 | |

FIG. 11 shows the results of the screening with the percentage of inhibition. The compounds that can inhibit *E. coli* topo I include, for example, suramin, NSC97419, and NSC668394.

Example 7—A T5 Exonuclease-Based HTS Assay for *E. coli* DNA Topoisomerase I

FIG. 12 shows a T5 exonuclease-based assay for identifying variola virus DNA topoisomerase 1 (vTopI) inhibitors. In the absence of inhibitors, the vTopI can convert the sc DNA molecule into the rx form, which can not be digested by T5 exonuclease. The rx DNA can then bind to the DNA staining dye, e.g., ethidium homodimer 1 (EthD1), leading to a high fluorescence. In the presence of the inhibitors, the sc DNA molecule is digested by T5 exonuclease into small DNA fragments, which results in low fluorescence in the presence of the DNA dye, e.g., EthD1.

The 50-compound library was again used to establish and validate the T5 exonuclease based HTS assay for vTopI. The compounds were added in the screening plate as indicated in Table 1. The screening results are shown in Table 6. The fluorescence was measured at $\lambda_{em}$ of 617 nm with $\lambda_{ex}$=528 nm using a plate reader. The number found in A2 indicates the result from suramin, a known inhibitor.

TABLE 6

HTS screening of 50-compound library for *E. coli* DNA topoisomerase 1 inhibitors.

|   | 1 | 2 | 3 | 4 | 5 | 6 | 7 |
|---|---|---|---|---|---|---|---|
| A | 1026 | 591 | 1311 | 1482 | 1340 | 1096 | 1194 |
| B | 1268 | 1321 | 1744 | 1189 | 1326 | 1210 | 893 |
| C | 1264 | 1243 | 1195 | 1456 | 1240 | 1354 | |
| D | 1299 | 1712 | 1214 | 1502 | 1439 | 1143 | |
| E | 966 | 1233 | 1203 | 1317 | 1162 | 1150 | |
| F | 1190 | 1336 | 1482 | 1028 | 1211 | 1359 | |
| G | 1649 | 1238 | 1434 | 1398 | 1535 | 1161 | |
| H | 1433 | 1711 | 1200 | 1430 | 1117 | 1255 | |

The results show that the compounds from the library, including enrofloxacin, suramin, and NSC97419, can inhibit Variola topo I.

Example 8—T5 Exonuclease-Based HTS Assays for Human DNA Topoisomerase I and II FIG. 13 shows T5 exonuclease-based assays for identifying inhibitors of human DNA topoisomerase 1 (HuTopI) and II (HuTopII). In the absence of inhibitors, the HuTopI or HuTopII can convert the sc DNA molecule into the rx form, which can not be digested by T5 exonuclease. The rx DNA can then bind to the DNA staining dye, e.g., ethidium homodimer 1 (EthD1), leading to a high fluorescence. In the presence of the inhibitors, the sc DNA molecule is digested by T5 exonuclease into small DNA fragments, which results in low fluorescence in the presence of the DNA dye, e.g., EthD1.

Compound NSC668394 is demonstrated as a new HuTopI inhibitor. FIG. 14 shows that compound NSC668394 strongly inhibits HuTopI activities with an IC50 of 5 μM. In contrast, NSC668394 did not inhibit MtbTopI (FIGS. 14B and D). These results show that NSC668394 specifically inhibits HuTopI.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. These examples should not be construed as limiting. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

We claim:

1. A method for identifying a DNA intercalator in a sample, comprising adding a circular double-stranded plasmid comprising two hairpin structures upon supercoiling, wherein the circular double-stranded plasmid does not comprise a fluorescent dye; adding a T5 exonuclease (T5E); adding a DNA-staining dye; and determining the presence or absence of the DNA intercalator based on fluorescence in the sample.

2. The method of claim 1, the circular double-stranded plasmid being in a supercoiled configuration.

3. The method of claim 1, the circular double-stranded plasmid being converted to a relaxed configuration in the presence of the DNA intercalator in the sample.

4. The method of claim 1, the circular double-stranded plasmid being pAB1.

5. The method of claim 1, the DNA-staining dye being Hoechest 33258, SYBR gold, ethidium bromide, EthD-1, or SYBR green.

6. The method of claim 1, the circular double-stranded plasmid comprising about 15 ATs to about 30 ATs.

7. The method of claim 1, the circular double-stranded plasmid comprising an adenosine-thymidine dinucleotide repeat (AT)n sequence, wherein n=21.

8. The method of claim 1, wherein a higher fluorescence in the sample than a control is indicative of the presence of the DNA intercalator, wherein the control comprises the circular supercoiled double-stranded plasmid in the absence of the DNA intercalator.

9. The method of claim 1, the circular double-stranded plasmid comprising at least one DNA endonuclease recognition site.

10. The method of claim 1, which comprises incubating T5E in the sample for at least 1 hour prior to adding the DNA-staining dye.

11. The method of claim 1, which further comprises adding ATP in the sample.

12. The method of claim 1, the sample being a sample in a high throughput screening (HTS) sample carrier.

* * * * *